(12) United States Patent
Greenhalgh et al.

(10) Patent No.: US 10,070,968 B2
(45) Date of Patent: Sep. 11, 2018

(54) SUPPORT DEVICE AND METHOD FOR USE

(71) Applicant: Flexmedex, LLC, Quakertown, PA (US)

(72) Inventors: E. Skott Greenhalgh, Gladwyne, PA (US); John-Paul Romano, Chalfont, PA (US)

(73) Assignee: Flexmedex, LLC, Quakertown, PA (US)

( * ) Notice: Subject to any disclaimer, the term of this patent is extended or adjusted under 35 U.S.C. 154(b) by 265 days.

(21) Appl. No.: 14/874,150

(22) Filed: Oct. 2, 2015

(65) Prior Publication Data

US 2016/0022429 A1 Jan. 28, 2016

Related U.S. Application Data

(63) Continuation of application No. 13/773,100, filed on Feb. 21, 2013, which is a continuation of application No. PCT/US2011/048992, filed on Aug. 24, 2011.

(Continued)

(51) Int. Cl.
*A61F 2/44* (2006.01)
*A61F 2/46* (2006.01)
(Continued)

(52) U.S. Cl.
CPC ............ *A61F 2/442* (2013.01); *A61F 2/4405* (2013.01); *A61F 2/4425* (2013.01); *A61F 2/4455* (2013.01); *A61F 2/4611* (2013.01); *A61F 2/30767* (2013.01); *A61F 2002/2817* (2013.01); *A61F 2002/2835* (2013.01); *A61F 2002/3054* (2013.01); *A61F 2002/3093* (2013.01); *A61F 2002/30378* (2013.01); *A61F 2002/30428* (2013.01); *A61F 2002/30462* (2013.01);
(Continued)

(58) Field of Classification Search
CPC ...... A61F 2/442; A61F 2/4425; A61F 2/4455; A61F 2/447; A61F 2/4611; A61F 2/44; A61F 2002/4415; A61F 2002/4475; A61B 17/7055
See application file for complete search history.

(56) References Cited

U.S. PATENT DOCUMENTS

| 646,119 A | 3/1900 | Clamer et al. |
| 4,204,531 A | 5/1980 | Aginsky |

(Continued)

FOREIGN PATENT DOCUMENTS

| DE | 19710392 | 7/1999 |
| WO | WO 2009/067568 | 5/2009 |

(Continued)

OTHER PUBLICATIONS

Gun Choi, Kim Jin-Sung, Pramod Lokhande, and Lee Sang-Ho. "Percutaneous Endoscopic Lumbar Discemtomy by Transiliac Approach." SPINE 34.12 (2009): E443-446.*

*Primary Examiner* — Matthew Lawson
*Assistant Examiner* — Amy Sipp
(74) *Attorney, Agent, or Firm* — Levine Bagade Han LLP

(57) ABSTRACT

Devices and methods for orthopedic support are disclosed. The device can have a first rigid section hingedly attached to a second rigid section. The device can be curved or rotated around obstructions along an access path to a target site. The device can be delivered to an intervertebral location in a patient.

2 Claims, 20 Drawing Sheets

Related U.S. Application Data

(60) Provisional application No. 61/376,626, filed on Aug. 24, 2010, provisional application No. 61/526,630, filed on Aug. 23, 2011.

(51) Int. Cl.
 *A61F 2/30* (2006.01)
 *A61F 2/28* (2006.01)

(52) U.S. Cl.
 CPC .............. *A61F 2002/30471* (2013.01); *A61F 2002/30528* (2013.01); *A61F 2002/30538* (2013.01); *A61F 2002/30594* (2013.01); *A61F 2002/30619* (2013.01); *A61F 2002/30629* (2013.01); *A61F 2002/30637* (2013.01); *A61F 2002/30685* (2013.01); *A61F 2002/30785* (2013.01); *A61F 2002/30914* (2013.01); *A61F 2002/30915* (2013.01); *A61F 2002/4415* (2013.01); *A61F 2002/4475* (2013.01); *A61F 2002/4485* (2013.01); *A61F 2002/4495* (2013.01); *A61F 2002/4677* (2013.01); *A61F 2310/00017* (2013.01); *A61F 2310/00023* (2013.01); *A61F 2310/00029* (2013.01); *A61F 2310/00071* (2013.01); *A61F 2310/00083* (2013.01); *A61F 2310/0097* (2013.01); *A61F 2310/00101* (2013.01); *A61F 2310/00131* (2013.01); *A61F 2310/00137* (2013.01); *A61F 2310/00155* (2013.01); *A61F 2310/00592* (2013.01); *A61F 2310/00796* (2013.01); *A61F 2310/00928* (2013.01); *A61F 2310/00952* (2013.01); *A61F 2310/00958* (2013.01); *A61F 2310/00976* (2013.01)

(56) References Cited

U.S. PATENT DOCUMENTS

| | | |
|---|---|---|
| 4,541,423 A | 9/1985 | Barber |
| 4,569,338 A | 2/1986 | Edwards |
| 4,636,217 A | 1/1987 | Ogilvie et al. |
| 4,653,489 A | 3/1987 | Tronzo |
| 4,716,893 A | 1/1988 | Fischer et al. |
| 4,725,264 A | 2/1988 | Glassman |
| 4,733,665 A | 3/1988 | Palmaz |
| 4,759,769 A | 7/1988 | Hedman et al. |
| 4,763,644 A | 8/1988 | Webb |
| 4,863,476 A | 9/1989 | Shepperd |
| 4,886,062 A | 12/1989 | Wiktor |
| 4,911,718 A | 3/1990 | Lee et al. |
| 4,932,975 A | 6/1990 | Main et al. |
| 4,941,466 A | 7/1990 | Romano |
| 4,969,888 A | 11/1990 | Scholten et al. |
| 5,007,909 A | 4/1991 | Rogozinski |
| 5,015,247 A | 5/1991 | Michelson |
| 5,026,373 A | 6/1991 | Ray et al. |
| 5,059,193 A | 10/1991 | Kuslich |
| 5,108,404 A | 4/1992 | Scholten et al. |
| 5,123,926 A | 6/1992 | Pisharodi |
| 5,139,480 A | 8/1992 | Hickle et al. |
| 5,171,278 A | 12/1992 | Pisharodi |
| 5,217,483 A | 6/1993 | Tower |
| 5,258,031 A | 11/1993 | Salib et al. |
| 5,306,278 A | 4/1994 | Dahl et al. |
| 5,324,295 A | 6/1994 | Shapiro, III |
| 5,342,348 A | 8/1994 | Kaplan |
| 5,345,927 A | 9/1994 | Bonutti |
| 5,390,683 A | 2/1995 | Pisharodi |
| 5,390,898 A | 2/1995 | Smedley et al. |
| 5,397,364 A | 3/1995 | Kozak et al. |
| 5,425,773 A | 6/1995 | Boyd et al. |
| 5,454,365 A | 10/1995 | Bonutti |
| 5,458,643 A | 10/1995 | Oka et al. |
| 5,480,442 A | 1/1996 | Bertagnoli |
| 5,484,384 A | 1/1996 | Fearnot |
| 5,496,365 A | 3/1996 | Sgro |
| 5,522,899 A | 6/1996 | Michelson |
| 5,534,002 A | 7/1996 | Brumfield et al. |
| 5,540,690 A | 7/1996 | Miller et al. |
| 5,549,679 A | 8/1996 | Kuslich |
| 5,554,191 A | 9/1996 | Lahille et al. |
| 5,556,413 A | 9/1996 | Lam |
| 5,562,736 A | 10/1996 | Ray et al. |
| 5,562,738 A | 10/1996 | Boyd et al. |
| 5,571,189 A | 11/1996 | Kuslich |
| 5,571,192 A | 11/1996 | Schonhoffer |
| 5,584,831 A | 12/1996 | McKay |
| 5,591,197 A | 1/1997 | Orth et al. |
| 5,593,409 A | 1/1997 | Michelson |
| 5,609,356 A | 3/1997 | Mossi |
| 5,609,635 A | 3/1997 | Michelson |
| 5,643,264 A | 7/1997 | Sherman et al. |
| 5,643,312 A | 7/1997 | Fischell et al. |
| 5,645,560 A | 7/1997 | Crocker et al. |
| 5,649,950 A | 7/1997 | Bourne et al. |
| 5,653,763 A | 8/1997 | Errico et al. |
| 5,658,335 A | 8/1997 | Allen |
| 5,665,122 A | 9/1997 | Kambin |
| 5,669,909 A | 9/1997 | Zdeblick et al. |
| 5,674,295 A | 10/1997 | Ray et al. |
| 5,683,394 A | 11/1997 | Rinner |
| 5,693,100 A | 12/1997 | Pisharodi |
| 5,702,449 A | 12/1997 | Mckay |
| 5,702,453 A | 12/1997 | Rabbe et al. |
| 5,741,253 A | 4/1998 | Michelson |
| 5,749,916 A | 5/1998 | Richelsoph |
| 5,772,661 A | 6/1998 | Michelson |
| 5,776,181 A | 7/1998 | Lee et al. |
| 5,776,197 A | 7/1998 | Rabbe et al. |
| 5,776,198 A | 7/1998 | Rabbe et al. |
| 5,776,199 A | 7/1998 | Michelson |
| 5,782,832 A | 7/1998 | Larsen et al. |
| 5,782,903 A | 7/1998 | Wiktor |
| 5,785,710 A | 7/1998 | Michelson |
| 5,800,520 A | 9/1998 | Fogarty et al. |
| 5,824,054 A | 10/1998 | Khosravi et al. |
| 5,824,093 A | 10/1998 | Ray et al. |
| 5,827,289 A | 10/1998 | Reiley et al. |
| 5,827,321 A | 10/1998 | Roubin et al. |
| 5,853,419 A | 12/1998 | Imran |
| 5,861,025 A | 1/1999 | Boudghene et al. |
| 5,863,284 A | 1/1999 | Klein |
| 5,865,848 A | 2/1999 | Baker |
| 5,895,387 A | 4/1999 | Guerrero et al. |
| 5,902,475 A | 5/1999 | Trozera et al. |
| 5,972,015 A | 10/1999 | Scribner et al. |
| 5,980,522 A | 11/1999 | Koros et al. |
| 5,980,550 A | 11/1999 | Eder et al. |
| 5,984,957 A | 11/1999 | Laptewicz et al. |
| 5,993,483 A | 11/1999 | Gianotti |
| 6,001,130 A | 12/1999 | Bryan et al. |
| 6,019,765 A | 2/2000 | Thornhill et al. |
| 6,019,792 A | 2/2000 | Cauthen |
| 6,022,376 A | 2/2000 | Assell et al. |
| 6,025,104 A | 2/2000 | Fuller et al. |
| 6,027,527 A | 2/2000 | Asano et al. |
| 6,036,719 A | 3/2000 | Meilus |
| 6,039,761 A | 3/2000 | Li et al. |
| 6,045,579 A | 4/2000 | Hochshuler et al. |
| 6,053,916 A | 4/2000 | Moore |
| 6,066,154 A | 5/2000 | Reiley et al. |
| 6,077,246 A | 6/2000 | Kullas et al. |
| 6,080,158 A | 6/2000 | Lin |
| 6,080,193 A | 6/2000 | Hochshuler et al. |
| 6,083,522 A | 7/2000 | Chu et al. |
| 6,086,610 A | 7/2000 | Duerig et al. |
| 6,090,143 A | 7/2000 | Meriwether et al. |
| 6,102,950 A | 8/2000 | Vaccaro |
| 6,113,628 A | 9/2000 | Borghi |
| 6,113,639 A | 9/2000 | Ray et al. |
| 6,126,689 A | 10/2000 | Brett |
| 6,127,597 A | 10/2000 | Beyar et al. |
| 6,129,763 A | 10/2000 | Chauvin et al. |

(56) References Cited

U.S. PATENT DOCUMENTS

| | | |
|---|---|---|
| 6,132,465 A | 10/2000 | Ray et al. |
| 6,140,452 A | 10/2000 | Felt et al. |
| 6,146,417 A | 11/2000 | Ischinger |
| 6,159,244 A | 12/2000 | Suddaby |
| 6,159,245 A | 12/2000 | Meriwether et al. |
| 6,168,616 B1 | 1/2001 | Brown |
| 6,171,312 B1 | 1/2001 | Beaty |
| 6,176,882 B1 | 1/2001 | Biedermann et al. |
| 6,179,874 B1 | 1/2001 | Cauthen |
| 6,183,506 B1 | 2/2001 | Penn et al. |
| 6,183,517 B1 | 2/2001 | Suddaby |
| 6,193,757 B1 | 2/2001 | Foley et al. |
| 6,206,910 B1 | 3/2001 | Berry et al. |
| 6,206,924 B1 | 3/2001 | Timm |
| 6,224,595 B1 | 5/2001 | Michelson |
| 6,224,603 B1 | 5/2001 | Marino |
| 6,224,604 B1 | 5/2001 | Suddaby |
| 6,224,607 B1 | 5/2001 | Michelson |
| 6,235,043 B1 | 5/2001 | Reiley et al. |
| 6,241,734 B1 | 6/2001 | Scribner et al. |
| 6,245,101 B1 | 6/2001 | Drasler et al. |
| 6,245,107 B1 | 6/2001 | Ferree |
| 6,248,110 B1 | 6/2001 | Reiley et al. |
| 6,280,456 B1 | 8/2001 | Scribner et al. |
| 6,287,332 B1 | 9/2001 | Bolz et al. |
| 6,293,967 B1 | 9/2001 | Shanley |
| 6,302,914 B1 | 10/2001 | Michelson |
| 6,332,895 B1 | 12/2001 | Suddaby |
| 6,371,989 B1 | 4/2002 | Chauvin et al. |
| 6,387,130 B1 | 5/2002 | Stone et al. |
| 6,395,031 B1 | 5/2002 | Foley et al. |
| 6,402,750 B1 | 6/2002 | Atkinson et al. |
| 6,402,785 B1 | 6/2002 | Zdeblick et al. |
| 6,409,765 B1 | 6/2002 | Bianchi et al. |
| 6,419,704 B1 | 7/2002 | Ferree |
| 6,419,705 B1 | 7/2002 | Erickson |
| 6,423,083 B2 | 7/2002 | Reiley et al. |
| 6,425,916 B1 | 7/2002 | Garrison et al. |
| 6,425,919 B1 | 7/2002 | Lambrecht |
| 6,428,569 B1 | 8/2002 | Brown |
| 6,432,107 B1 | 8/2002 | Ferree |
| 6,436,098 B1 | 8/2002 | Michelson |
| 6,436,140 B1 | 8/2002 | Liu et al. |
| 6,440,168 B1 | 8/2002 | Cauthen |
| 6,447,544 B1 | 9/2002 | Michelson |
| 6,447,546 B1 | 9/2002 | Bramlet et al. |
| 6,447,547 B1 | 9/2002 | Michelson |
| 6,451,025 B1 | 9/2002 | Jervis |
| 6,454,804 B1 | 9/2002 | Ferree |
| 6,468,301 B1 | 10/2002 | Amplatz et al. |
| 6,468,302 B2 | 10/2002 | Cox et al. |
| 6,478,823 B1 | 11/2002 | Michelson |
| 6,482,235 B1 | 11/2002 | Lambrecht et al. |
| 6,488,710 B2 | 12/2002 | Besselink |
| 6,491,724 B1 | 12/2002 | Ferree |
| 6,494,883 B1 | 12/2002 | Ferree |
| 6,508,820 B2 | 1/2003 | Bales |
| 6,508,839 B1 | 1/2003 | Lambrecht et al. |
| 6,514,255 B1 | 2/2003 | Ferree |
| 6,520,991 B2 | 2/2003 | Huene |
| 6,533,817 B1 | 3/2003 | Norton et al. |
| 6,551,342 B1 | 4/2003 | Shen et al. |
| 6,554,833 B2 | 4/2003 | Levy et al. |
| 6,562,074 B2 | 5/2003 | Gerbec et al. |
| 6,582,431 B1 | 6/2003 | Ray |
| 6,582,467 B1 | 6/2003 | Teitelbaum et al. |
| 6,585,770 B1 | 7/2003 | White et al. |
| 6,592,589 B2 | 7/2003 | Hajianpour |
| 6,592,625 B2 | 7/2003 | Cauthen |
| 6,595,998 B2 | 7/2003 | Johnson et al. |
| 6,602,291 B1 | 8/2003 | Ray et al. |
| 6,607,530 B1 | 8/2003 | Carl et al. |
| 6,607,544 B1 | 8/2003 | Boucher et al. |
| 6,613,054 B2 | 9/2003 | Scribner et al. |
| 6,623,505 B2 | 9/2003 | Scribner et al. |
| 6,641,587 B2 | 11/2003 | Scribner et al. |
| 6,641,614 B1 | 11/2003 | Wagner et al. |
| 6,645,213 B2 | 11/2003 | Sand et al. |
| 6,645,247 B2 | 11/2003 | Ferree |
| 6,648,917 B2 | 11/2003 | Gerbec et al. |
| 6,648,918 B2 | 11/2003 | Ferree |
| 6,648,920 B2 | 11/2003 | Ferree |
| 6,652,584 B2 | 11/2003 | Michelson |
| 6,656,178 B1 | 12/2003 | Veldhuizen et al. |
| 6,663,647 B2 | 12/2003 | Reiley et al. |
| 6,666,891 B2 | 12/2003 | Boehm et al. |
| 6,676,665 B2 | 1/2004 | Foley et al. |
| 6,679,915 B1 | 1/2004 | Cauthen |
| 6,685,695 B2 | 2/2004 | Ferree |
| 6,695,760 B1 | 2/2004 | Winkler et al. |
| 6,706,068 B2 | 3/2004 | Ferree |
| 6,706,070 B1 | 3/2004 | Wagner et al. |
| 6,709,458 B2 | 3/2004 | Michelson |
| 6,712,853 B2 | 3/2004 | Kuslich |
| 6,716,216 B1 | 4/2004 | Boucher et al. |
| 6,716,247 B2 | 4/2004 | Michelson |
| 6,719,773 B1 | 4/2004 | Boucher et al. |
| 6,723,126 B1 | 4/2004 | Berry |
| 6,726,691 B2 | 4/2004 | Osorio et al. |
| 6,733,535 B2 | 5/2004 | Michelson |
| 6,740,090 B1 | 5/2004 | Cragg et al. |
| 6,743,255 B2 | 6/2004 | Ferree |
| 6,746,451 B2 | 6/2004 | Middleton et al. |
| 6,758,863 B2 | 7/2004 | Estes et al. |
| 6,793,656 B1 | 9/2004 | Mathews |
| 6,793,679 B2 | 9/2004 | Michelson |
| 6,808,537 B2 | 10/2004 | Michelson |
| 6,814,756 B1 | 11/2004 | Michelson |
| 6,830,589 B2 | 12/2004 | Erickson |
| 6,852,115 B2 | 2/2005 | Kinnett |
| 6,852,123 B2 | 2/2005 | Brown |
| 6,852,129 B2 | 2/2005 | Gerbec et al. |
| 6,863,673 B2 | 3/2005 | Gerbec et al. |
| 6,893,464 B2 | 5/2005 | Kiester |
| 6,899,716 B2 | 5/2005 | Cragg |
| 6,899,719 B2 | 5/2005 | Reiley et al. |
| 6,921,264 B2 | 7/2005 | Mayer et al. |
| 6,923,813 B2 | 8/2005 | Phillips et al. |
| 6,923,830 B2 | 8/2005 | Michelson |
| 6,936,065 B2 | 8/2005 | Khan et al. |
| 6,936,070 B1 | 8/2005 | Muhanna |
| 6,948,223 B2 | 9/2005 | Shortt |
| 6,953,477 B2 | 10/2005 | Berry |
| 6,955,691 B2 | 10/2005 | Chae et al. |
| 6,960,215 B2 | 11/2005 | Olson et al. |
| 6,962,606 B2 | 11/2005 | Michelson |
| 6,981,981 B2 | 1/2006 | Reiley et al. |
| 6,988,710 B2 | 1/2006 | Igarashi |
| 7,008,453 B1 | 3/2006 | Michelson |
| 7,018,415 B1 | 3/2006 | McKay |
| 7,018,416 B2 | 3/2006 | Hanson et al. |
| 7,056,321 B2 | 6/2006 | Pagliuca et al. |
| 7,060,073 B2 | 6/2006 | Frey et al. |
| 7,066,961 B2 | 6/2006 | Michelson |
| 7,077,864 B2 | 7/2006 | Byrd et al. |
| 7,087,055 B2 | 8/2006 | Lim et al. |
| 7,094,257 B2 | 8/2006 | Mujwid et al. |
| 7,097,648 B1 | 8/2006 | Globerman et al. |
| 7,112,206 B2 | 9/2006 | Michelson |
| 7,118,598 B2 | 10/2006 | Michelson |
| 7,135,043 B2 | 11/2006 | Nakahara et al. |
| 7,166,110 B2 | 1/2007 | Yundt |
| 7,201,751 B2 | 4/2007 | Zucherman et al. |
| 7,201,775 B2 | 4/2007 | Gorensek et al. |
| 7,204,853 B2 | 4/2007 | Gordon et al. |
| 7,211,112 B2 | 5/2007 | Baynham et al. |
| 7,223,292 B2 | 5/2007 | Messerli et al. |
| 7,226,475 B2 | 6/2007 | Lenz et al. |
| 7,226,481 B2 | 6/2007 | Kuslich |
| 7,226,483 B2 | 6/2007 | Gerber et al. |
| 7,238,186 B2 | 7/2007 | Zdeblick et al. |
| 7,241,297 B2 | 7/2007 | Shaolian et al. |
| 7,241,303 B2 | 7/2007 | Reiss et al. |
| 7,300,440 B2 | 11/2007 | Zdeblick et al. |

(56) References Cited

U.S. PATENT DOCUMENTS

| | | |
|---|---|---|
| 7,309,338 B2 | 12/2007 | Cragg |
| 7,311,713 B2 | 12/2007 | Johnson et al. |
| 7,316,714 B2 | 1/2008 | Gordon et al. |
| 7,318,826 B2 | 1/2008 | Teitelbaum et al. |
| 7,396,360 B2 | 7/2008 | Lieberman |
| 7,431,735 B2 | 10/2008 | Liu et al. |
| 7,452,371 B2 | 11/2008 | Pavcnik et al. |
| 7,488,337 B2 | 2/2009 | Saab et al. |
| 7,503,933 B2 | 3/2009 | Michelson |
| 7,507,241 B2 | 3/2009 | Levy et al. |
| 7,582,106 B2 | 9/2009 | Teitelbaum et al. |
| 7,601,172 B2 | 10/2009 | Segal et al. |
| 7,618,457 B2 | 11/2009 | Hudgins |
| 7,621,950 B1 | 11/2009 | Globerman et al. |
| 7,625,395 B2 | 12/2009 | Mückter |
| 7,628,807 B2 | 12/2009 | Flanagan |
| 7,722,674 B1 | 5/2010 | Grotz |
| 7,749,228 B2 | 7/2010 | Lieberman |
| 7,763,028 B2 | 7/2010 | Lim et al. |
| 7,771,463 B2 | 8/2010 | Ton et al. |
| 7,828,849 B2 | 11/2010 | Lim |
| 7,837,734 B2 | 11/2010 | Zucherman et al. |
| 7,867,233 B2 | 1/2011 | Shaolian et al. |
| 7,875,035 B2 | 1/2011 | Boucher et al. |
| 7,879,036 B2 | 2/2011 | Biedermann et al. |
| 7,879,082 B2 | 2/2011 | Brown |
| 8,007,498 B2 | 8/2011 | Mische |
| 8,034,110 B2 | 10/2011 | Garner et al. |
| 8,062,375 B2 | 11/2011 | Glerum et al. |
| 8,105,382 B2 | 1/2012 | Olmos et al. |
| 8,142,507 B2 | 3/2012 | McGuckin |
| 8,162,943 B2 | 4/2012 | Justin et al. |
| 8,206,423 B2 | 6/2012 | Siegal |
| 8,246,622 B2 | 8/2012 | Siegal et al. |
| 8,262,737 B2 | 9/2012 | Bagga et al. |
| 8,425,570 B2 | 4/2013 | Reiley |
| 8,465,524 B2 | 6/2013 | Siegal |
| 8,486,149 B2 | 7/2013 | Saidha et al. |
| 8,512,408 B2 | 8/2013 | Miller et al. |
| 8,518,120 B2 | 8/2013 | Glerum et al. |
| 8,551,171 B2 | 10/2013 | Johnson et al. |
| 8,556,979 B2 | 10/2013 | Glerum et al. |
| 8,579,912 B2 | 11/2013 | Isaza et al. |
| 8,591,582 B2 | 11/2013 | Anderson et al. |
| 8,672,968 B2 | 3/2014 | Stone et al. |
| 8,672,977 B2 | 3/2014 | Siegal et al. |
| 8,679,183 B2 | 3/2014 | Glerum et al. |
| 8,685,098 B2 | 4/2014 | Glerum et al. |
| 8,709,042 B2 | 4/2014 | Greenhalgh et al. |
| 8,777,993 B2 | 7/2014 | Siegal et al. |
| 8,845,731 B2 | 9/2014 | Weiman |
| 8,845,734 B2 | 9/2014 | Weiman |
| 9,216,095 B2 | 12/2015 | Glerum et al. |
| 9,402,739 B2 | 8/2016 | Weiman et al. |
| 9,408,708 B2 | 8/2016 | Greenhalgh |
| 9,510,885 B2 | 12/2016 | Burger et al. |
| 2001/0007956 A1 | 7/2001 | Letac et al. |
| 2001/0034552 A1 | 10/2001 | Young et al. |
| 2002/0007218 A1 | 1/2002 | Cauthen |
| 2002/0010511 A1 | 1/2002 | Michelson |
| 2002/0022887 A1 | 2/2002 | Huene |
| 2002/0032444 A1 | 3/2002 | Mische |
| 2002/0038767 A1 | 4/2002 | Trozera |
| 2002/0052656 A1 | 5/2002 | Michelson |
| 2002/0068911 A1 | 6/2002 | Chan |
| 2002/0068939 A1 | 6/2002 | Levy et al. |
| 2002/0068975 A1 | 6/2002 | Teitelbaum et al. |
| 2002/0068976 A1 | 6/2002 | Jackson |
| 2002/0068977 A1 | 6/2002 | Jackson |
| 2002/0082598 A1 | 6/2002 | Teitelbaum |
| 2002/0082600 A1 | 6/2002 | Shaolian et al. |
| 2002/0091390 A1 | 7/2002 | Michelson |
| 2002/0095155 A1 | 7/2002 | Michelson |
| 2002/0099378 A1 | 7/2002 | Michelson |
| 2002/0111688 A1 | 8/2002 | Cauthen |
| 2002/0120337 A1 | 8/2002 | Cauthen |
| 2002/0123807 A1 | 9/2002 | Cauthen |
| 2002/0128713 A1 | 9/2002 | Ferree |
| 2002/0138077 A1 | 9/2002 | Ferree |
| 2002/0138133 A1 | 9/2002 | Lenz et al. |
| 2002/0138144 A1 | 9/2002 | Michelson |
| 2002/0143401 A1 | 10/2002 | Michelson |
| 2002/0151896 A1 | 10/2002 | Ferree |
| 2002/0151980 A1 | 10/2002 | Cauthen |
| 2002/0156530 A1 | 10/2002 | Lambrecht et al. |
| 2002/0161367 A1 | 10/2002 | Ferree |
| 2002/0161373 A1 | 10/2002 | Osorio et al. |
| 2002/0165542 A1 | 11/2002 | Ferree |
| 2002/0189622 A1 | 12/2002 | Cauthen et al. |
| 2002/0198526 A1 | 12/2002 | Shaolian et al. |
| 2003/0004511 A1 | 1/2003 | Ferree |
| 2003/0004574 A1 | 1/2003 | Ferree |
| 2003/0009227 A1 | 1/2003 | Lambrecht et al. |
| 2003/0014118 A1 | 1/2003 | Lambrecht et al. |
| 2003/0026788 A1 | 2/2003 | Ferree |
| 2003/0032963 A1 | 2/2003 | Reiss et al. |
| 2003/0040796 A1 | 2/2003 | Ferree |
| 2003/0040798 A1 | 2/2003 | Michelson |
| 2003/0050701 A1 | 3/2003 | Michelson |
| 2003/0065394 A1 | 4/2003 | Michelson |
| 2003/0065396 A1 | 4/2003 | Michelson |
| 2003/0074076 A1 | 4/2003 | Ferree et al. |
| 2003/0078579 A1 | 4/2003 | Ferree |
| 2003/0088249 A1 | 5/2003 | Furderer |
| 2003/0120345 A1 | 6/2003 | Cauthen |
| 2003/0125748 A1 | 7/2003 | Li et al. |
| 2003/0125807 A1 | 7/2003 | Lambrecht et al. |
| 2003/0135220 A1 | 7/2003 | Cauthen |
| 2003/0135279 A1 | 7/2003 | Michelson |
| 2003/0149482 A1 | 8/2003 | Michelson |
| 2003/0153976 A1 | 8/2003 | Cauthen et al. |
| 2003/0158553 A1 | 8/2003 | Michelson |
| 2003/0158604 A1 | 8/2003 | Cauthen et al. |
| 2003/0163200 A1 | 8/2003 | Cauthen |
| 2003/0171813 A1 | 9/2003 | Kiester |
| 2003/0181979 A1 | 9/2003 | Ferree |
| 2003/0181980 A1 | 9/2003 | Berry et al. |
| 2003/0181983 A1 | 9/2003 | Cauthen |
| 2003/0187507 A1 | 10/2003 | Cauthen |
| 2003/0187508 A1 | 10/2003 | Cauthen |
| 2003/0191536 A1 | 10/2003 | Ferree |
| 2003/0195514 A1 | 10/2003 | Trieu et al. |
| 2003/0195630 A1 | 10/2003 | Ferree |
| 2003/0195631 A1 | 10/2003 | Ferree |
| 2003/0199979 A1 | 10/2003 | Mcguckin |
| 2003/0199981 A1 | 10/2003 | Ferree |
| 2003/0204189 A1 | 10/2003 | Cragg |
| 2003/0204260 A1 | 10/2003 | Ferree |
| 2003/0208270 A9 | 11/2003 | Michelson |
| 2003/0220643 A1 | 11/2003 | Ferree |
| 2003/0220650 A1 | 11/2003 | Major et al. |
| 2003/0220690 A1 | 11/2003 | Cauthen |
| 2003/0220693 A1 | 11/2003 | Cauthen |
| 2003/0220694 A1 | 11/2003 | Cauthen |
| 2003/0233097 A1 | 12/2003 | Ferree |
| 2003/0233148 A1 | 12/2003 | Ferree |
| 2003/0236520 A1 | 12/2003 | Lim et al. |
| 2004/0002759 A1 | 1/2004 | Ferree |
| 2004/0002760 A1 | 1/2004 | Boyd et al. |
| 2004/0002769 A1 | 1/2004 | Ferree |
| 2004/0006341 A1 | 1/2004 | Shaolian et al. |
| 2004/0006344 A1 | 1/2004 | Nguyen et al. |
| 2004/0010315 A1 | 1/2004 | Song |
| 2004/0010318 A1 | 1/2004 | Ferree |
| 2004/0019386 A1 | 1/2004 | Ferree |
| 2004/0024400 A1 | 2/2004 | Michelson |
| 2004/0024459 A1 | 2/2004 | Ferree |
| 2004/0024460 A1 | 2/2004 | Ferree |
| 2004/0024461 A1 | 2/2004 | Ferree |
| 2004/0024462 A1 | 2/2004 | Ferree et al. |
| 2004/0024469 A1 | 2/2004 | Ferree |
| 2004/0024471 A1 | 2/2004 | Ferree |
| 2004/0028718 A1 | 2/2004 | Ferree |
| 2004/0030387 A1 | 2/2004 | Landry et al. |

(56) References Cited

U.S. PATENT DOCUMENTS

| | | |
|---|---|---|
| 2004/0030389 A1 | 2/2004 | Ferree |
| 2004/0030390 A1 | 2/2004 | Ferree |
| 2004/0030391 A1 | 2/2004 | Ferree |
| 2004/0030398 A1 | 2/2004 | Ferree |
| 2004/0034357 A1 | 2/2004 | Beane et al. |
| 2004/0044410 A1 | 3/2004 | Ferree et al. |
| 2004/0049289 A1 | 3/2004 | Tordy et al. |
| 2004/0059418 A1 | 3/2004 | Mckay et al. |
| 2004/0059419 A1 | 3/2004 | Michelson |
| 2004/0059429 A1 | 3/2004 | Amin et al. |
| 2004/0068259 A1 | 4/2004 | Michelson |
| 2004/0082954 A1 | 4/2004 | Teitelbaum et al. |
| 2004/0082961 A1 | 4/2004 | Teitelbaum |
| 2004/0087947 A1 | 5/2004 | Lim et al. |
| 2004/0087950 A1 | 5/2004 | Teitelbaum |
| 2004/0092933 A1 | 5/2004 | Shaolian et al. |
| 2004/0092946 A1 | 5/2004 | Bagga et al. |
| 2004/0092988 A1* | 5/2004 | Shaolian ............ A61B 17/1617 606/167 |
| 2004/0097927 A1 | 5/2004 | Yeung et al. |
| 2004/0102848 A1 | 5/2004 | Michelson |
| 2004/0111108 A1 | 6/2004 | Farnan |
| 2004/0133229 A1 | 7/2004 | Lambrecht et al. |
| 2004/0133280 A1 | 7/2004 | Trieu |
| 2004/0138673 A1 | 7/2004 | Lambrecht et al. |
| 2004/0153064 A1 | 8/2004 | Foley et al. |
| 2004/0153065 A1 | 8/2004 | Lim |
| 2004/0153146 A1 | 8/2004 | Lashinski et al. |
| 2004/0167625 A1 | 8/2004 | Beyar et al. |
| 2004/0172019 A1 | 9/2004 | Ferree |
| 2005/0010292 A1 | 1/2005 | Carrasco |
| 2005/0015152 A1 | 1/2005 | Sweeney |
| 2005/0022839 A1 | 2/2005 | Savas et al. |
| 2005/0033431 A1 | 2/2005 | Gordon et al. |
| 2005/0038512 A1 | 2/2005 | Michelson |
| 2005/0043796 A1 | 2/2005 | Grant et al. |
| 2005/0070911 A1 | 3/2005 | Carrison et al. |
| 2005/0080422 A1 | 4/2005 | Otte et al. |
| 2005/0085910 A1 | 4/2005 | Sweeney |
| 2005/0107863 A1 | 5/2005 | Brown |
| 2005/0113919 A1 | 5/2005 | Cragg et al. |
| 2005/0113928 A1 | 5/2005 | Cragg et al. |
| 2005/0119561 A1 | 6/2005 | Kienzle |
| 2005/0143827 A1 | 6/2005 | Globerman et al. |
| 2005/0182463 A1 | 8/2005 | Hunter et al. |
| 2005/0187558 A1 | 8/2005 | Johnson et al. |
| 2005/0209698 A1 | 9/2005 | Gordon et al. |
| 2005/0228391 A1 | 10/2005 | Levy et al. |
| 2005/0228472 A1 | 10/2005 | Case et al. |
| 2005/0240188 A1 | 10/2005 | Chow et al. |
| 2005/0249776 A1 | 11/2005 | Chen et al. |
| 2005/0261683 A1 | 11/2005 | Veldhuizen et al. |
| 2005/0261695 A1 | 11/2005 | Cragg et al. |
| 2005/0261768 A1 | 11/2005 | Trieu |
| 2005/0261781 A1 | 11/2005 | Sennett et al. |
| 2005/0278023 A1 | 12/2005 | Zwirkoski |
| 2005/0278026 A1 | 12/2005 | Gordon et al. |
| 2005/0278036 A1 | 12/2005 | Leonard et al. |
| 2006/0004455 A1 | 1/2006 | Leonard et al. |
| 2006/0015184 A1 | 1/2006 | Winterbottom et al. |
| 2006/0022180 A1 | 2/2006 | Selness |
| 2006/0036241 A1 | 2/2006 | Siegal |
| 2006/0036273 A1 | 2/2006 | Siegal |
| 2006/0052788 A1 | 3/2006 | Thelen et al. |
| 2006/0052870 A1 | 3/2006 | Ferree |
| 2006/0058807 A1 | 3/2006 | Landry et al. |
| 2006/0058876 A1 | 3/2006 | Mckinley |
| 2006/0058880 A1 | 3/2006 | Wysocki et al. |
| 2006/0079898 A1 | 4/2006 | Ainsworth et al. |
| 2006/0085069 A1 | 4/2006 | Kim |
| 2006/0085070 A1 | 4/2006 | Kim |
| 2006/0089715 A1 | 4/2006 | Truckai et al. |
| 2006/0095123 A1 | 5/2006 | Flanagan |
| 2006/0100706 A1 | 5/2006 | Shadduck et al. |
| 2006/0106460 A1 | 5/2006 | Messerli et al. |
| 2006/0122701 A1 | 6/2006 | Kiester |
| 2006/0129244 A1 | 6/2006 | Ensign |
| 2006/0142858 A1 | 6/2006 | Colleran et al. |
| 2006/0142859 A1 | 6/2006 | Mcluen |
| 2006/0149239 A1 | 7/2006 | Winslow et al. |
| 2006/0149349 A1 | 7/2006 | Garbe |
| 2006/0149385 A1 | 7/2006 | Mckay |
| 2006/0155379 A1 | 7/2006 | Heneveld et al. |
| 2006/0161261 A1 | 7/2006 | Brown et al. |
| 2006/0178694 A1 | 8/2006 | Greenhalgh et al. |
| 2006/0184188 A1 | 8/2006 | Li et al. |
| 2006/0184248 A1 | 8/2006 | Edidin et al. |
| 2006/0189999 A1 | 8/2006 | Zwirkoski |
| 2006/0200166 A1 | 9/2006 | Hanson et al. |
| 2006/0206207 A1 | 9/2006 | Dryer et al. |
| 2006/0235414 A1 | 10/2006 | Lim et al. |
| 2006/0235423 A1 | 10/2006 | Cantu |
| 2006/0241764 A1 | 10/2006 | Michelson |
| 2006/0253201 A1 | 11/2006 | Mcluen |
| 2006/0264968 A1 | 11/2006 | Frey et al. |
| 2006/0265077 A1 | 11/2006 | Zwirkoski |
| 2006/0271061 A1 | 11/2006 | Beyar et al. |
| 2006/0287725 A1 | 12/2006 | Miller |
| 2006/0287726 A1 | 12/2006 | Segal et al. |
| 2006/0287727 A1 | 12/2006 | Segal et al. |
| 2006/0287729 A1 | 12/2006 | Segal et al. |
| 2006/0287730 A1 | 12/2006 | Segal et al. |
| 2007/0027363 A1 | 2/2007 | Gannoe et al. |
| 2007/0032791 A1 | 2/2007 | Greenhalgh |
| 2007/0043440 A1 | 2/2007 | William et al. |
| 2007/0055375 A1 | 3/2007 | Ferree |
| 2007/0055377 A1 | 3/2007 | Hanson et al. |
| 2007/0067034 A1 | 3/2007 | Chirico et al. |
| 2007/0067035 A1 | 3/2007 | Falahee |
| 2007/0093897 A1 | 4/2007 | Gerbec et al. |
| 2007/0093899 A1 | 4/2007 | Dutoit et al. |
| 2007/0112428 A1 | 5/2007 | Lancial |
| 2007/0118222 A1 | 5/2007 | Lang |
| 2007/0123877 A1 | 5/2007 | Goldin et al. |
| 2007/0123986 A1 | 5/2007 | Schaller |
| 2007/0162044 A1 | 7/2007 | Marino |
| 2007/0162135 A1 | 7/2007 | Segal et al. |
| 2007/0173824 A1 | 7/2007 | Rosen |
| 2007/0173830 A1 | 7/2007 | Rosen |
| 2007/0173939 A1 | 7/2007 | Kim et al. |
| 2007/0173940 A1 | 7/2007 | Hestad et al. |
| 2007/0208423 A1 | 9/2007 | Messerli et al. |
| 2007/0213717 A1 | 9/2007 | Trieu et al. |
| 2007/0225703 A1 | 9/2007 | Schmitz et al. |
| 2007/0233260 A1 | 10/2007 | Cragg |
| 2007/0239162 A1 | 10/2007 | Bhatnagar et al. |
| 2007/0244485 A1 | 10/2007 | Greenhalgh et al. |
| 2007/0255408 A1 | 11/2007 | Castleman et al. |
| 2007/0255409 A1 | 11/2007 | Dickson et al. |
| 2007/0260270 A1* | 11/2007 | Assell ................. A61B 17/025 606/171 |
| 2007/0260315 A1 | 11/2007 | Foley et al. |
| 2007/0270956 A1 | 11/2007 | Heinz |
| 2007/0270968 A1 | 11/2007 | Baynham et al. |
| 2007/0276377 A1 | 11/2007 | Yundt |
| 2007/0282342 A1 | 12/2007 | Niederberger et al. |
| 2007/0288028 A1 | 12/2007 | Gorensek et al. |
| 2008/0015694 A1 | 1/2008 | Tribus |
| 2008/0021558 A1 | 1/2008 | Thramann |
| 2008/0021559 A1 | 1/2008 | Thramann |
| 2008/0071356 A1 | 3/2008 | Greenhalgh et al. |
| 2008/0077150 A1 | 3/2008 | Nguyen |
| 2008/0082162 A1 | 4/2008 | Boismier et al. |
| 2008/0124865 A1 | 5/2008 | Lutze et al. |
| 2008/0125865 A1 | 5/2008 | Abdelgany |
| 2008/0133012 A1 | 6/2008 | McGuckin |
| 2008/0140082 A1 | 6/2008 | Erdem et al. |
| 2008/0140179 A1 | 6/2008 | Ladisa |
| 2008/0140207 A1 | 6/2008 | Olmos et al. |
| 2008/0147193 A1 | 6/2008 | Matthis et al. |
| 2008/0147194 A1 | 6/2008 | Grotz et al. |
| 2008/0183204 A1 | 7/2008 | Greenhalgh et al. |
| 2008/0188941 A1 | 8/2008 | Grotz |
| 2008/0208255 A1 | 8/2008 | Siegal |

(56) References Cited

U.S. PATENT DOCUMENTS

| | | |
|---|---|---|
| 2008/0221687 A1 | 9/2008 | Viker |
| 2008/0243254 A1 | 10/2008 | Butler |
| 2008/0243255 A1 | 10/2008 | Butler et al. |
| 2008/0249625 A1 | 10/2008 | Waugh et al. |
| 2008/0249628 A1 | 10/2008 | Altarac et al. |
| 2008/0294205 A1 | 11/2008 | Greenhalgh et al. |
| 2008/0312743 A1 | 12/2008 | Vila et al. |
| 2008/0312744 A1 | 12/2008 | Vresilovic et al. |
| 2009/0005871 A1 | 1/2009 | White et al. |
| 2009/0018524 A1 | 1/2009 | Greenhalgh et al. |
| 2009/0024204 A1 | 1/2009 | Greenhalgh et al. |
| 2009/0024217 A1 | 1/2009 | Levy et al. |
| 2009/0054991 A1 | 2/2009 | Biyani et al. |
| 2009/0076511 A1 | 3/2009 | Osman |
| 2009/0143859 A1 | 6/2009 | McClellan et al. |
| 2009/0149956 A1 | 6/2009 | Greenhalgh et al. |
| 2009/0163918 A1 | 6/2009 | Levy et al. |
| 2009/0177207 A1 | 7/2009 | Schaller |
| 2009/0182336 A1 | 7/2009 | Brenzel et al. |
| 2009/0182431 A1 | 7/2009 | Butler et al. |
| 2009/0198338 A1 | 8/2009 | Phan |
| 2009/0234398 A1 | 9/2009 | Chirico et al. |
| 2009/0240335 A1 | 9/2009 | Arcenio et al. |
| 2009/0318928 A1 | 12/2009 | Purcell et al. |
| 2010/0004750 A1 | 1/2010 | Segal et al. |
| 2010/0004751 A1 | 1/2010 | Segal et al. |
| 2010/0016905 A1 | 1/2010 | Greenhalgh et al. |
| 2010/0082109 A1 | 4/2010 | Greenhalgh et al. |
| 2010/0125274 A1 | 5/2010 | Greenhalgh et al. |
| 2010/0168862 A1 | 7/2010 | Edie et al. |
| 2010/0262147 A1 | 10/2010 | Siegal et al. |
| 2010/0292796 A1 | 11/2010 | Greenhalgh et al. |
| 2010/0324560 A1 | 12/2010 | Suda |
| 2011/0009869 A1 | 1/2011 | Marino et al. |
| 2011/0009969 A1 | 1/2011 | Puno |
| 2011/0029083 A1 | 2/2011 | Hynes et al. |
| 2011/0046737 A1 | 2/2011 | Teisen |
| 2011/0054621 A1 | 3/2011 | Lim |
| 2011/0087296 A1 | 4/2011 | Reiley et al. |
| 2011/0106260 A1 | 5/2011 | Laurence et al. |
| 2011/0118785 A1 | 5/2011 | Reiley |
| 2011/0125266 A1 * | 5/2011 | Rodgers .......... A61F 2/447 623/17.11 |
| 2011/0153019 A1 | 6/2011 | Siegal |
| 2011/0166575 A1 | 7/2011 | Assell et al. |
| 2011/0184519 A1 | 7/2011 | Trieu |
| 2011/0230884 A1 | 9/2011 | Mantzaris et al. |
| 2011/0230966 A1 | 9/2011 | Trieu |
| 2011/0257684 A1 | 10/2011 | Sankaran |
| 2011/0282387 A1 | 11/2011 | Suh et al. |
| 2011/0319898 A1 | 12/2011 | O'Neil et al. |
| 2011/0320000 A1 | 12/2011 | O'Neil et al. |
| 2012/0004731 A1 | 1/2012 | Viker |
| 2012/0029518 A1 | 2/2012 | Blackwell et al. |
| 2012/0071962 A1 | 3/2012 | Huang et al. |
| 2012/0071980 A1 | 3/2012 | Purcell et al. |
| 2013/0035723 A1 | 2/2013 | Donner |
| 2013/0053852 A1 | 2/2013 | Greenhalgh et al. |
| 2013/0085535 A1 | 4/2013 | Greenhalgh et al. |
| 2013/0138214 A1 | 5/2013 | Greenhalgh et al. |
| 2013/0173004 A1 | 7/2013 | Greenhalgh et al. |
| 2013/0304224 A1 | 11/2013 | Schmidt et al. |
| 2014/0088713 A1 | 3/2014 | Greenhalgh et al. |
| 2014/0155980 A1 | 6/2014 | Turjman et al. |

FOREIGN PATENT DOCUMENTS

| | | |
|---|---|---|
| WO | WO 2012/040272 | 3/2012 |
| WO | WO 2012/083173 | 6/2012 |

* cited by examiner

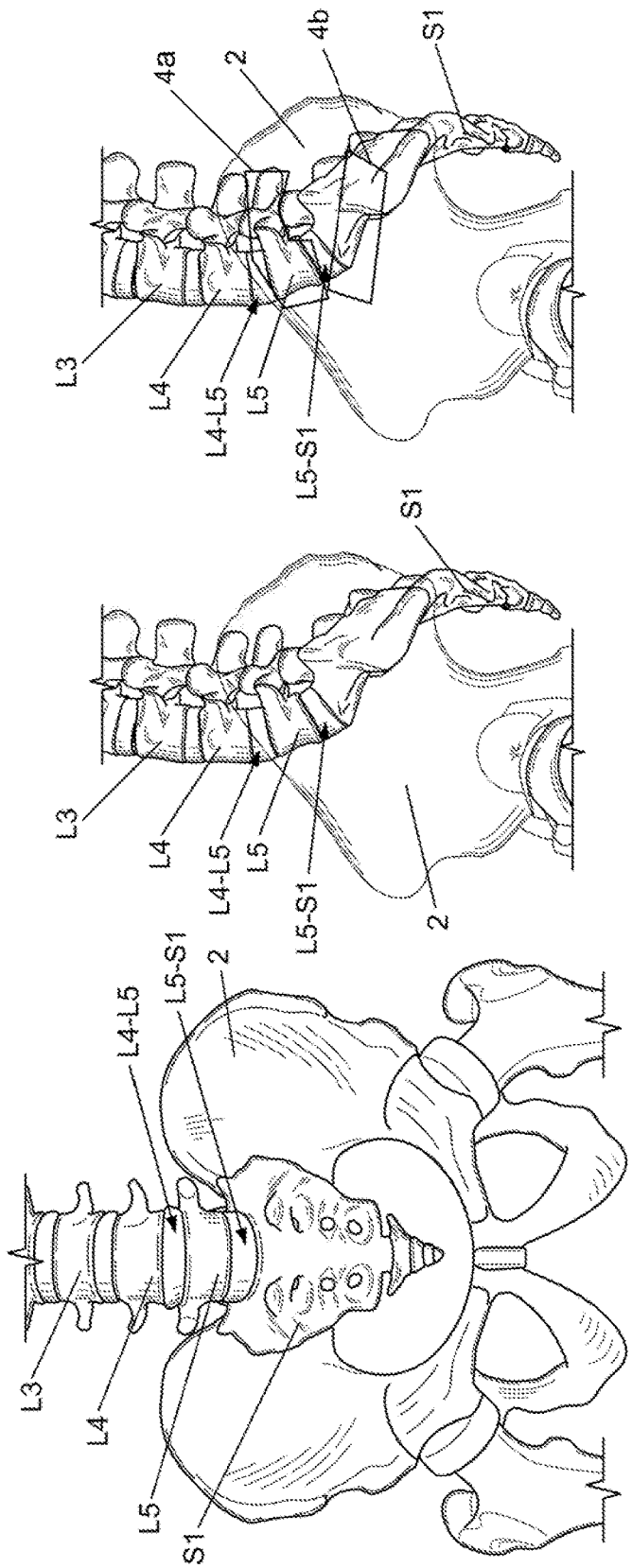

NOT INVENTION

NOT INVENTION

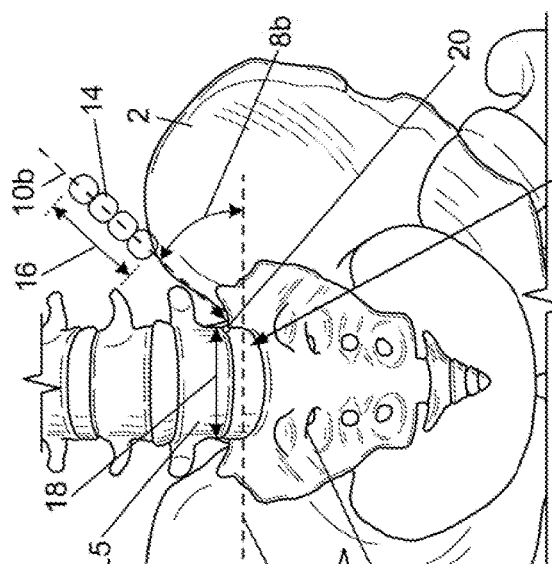
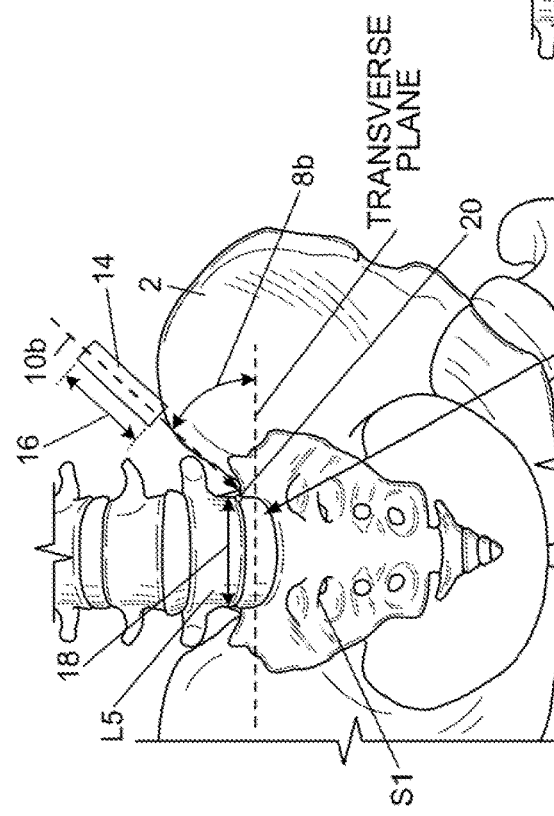
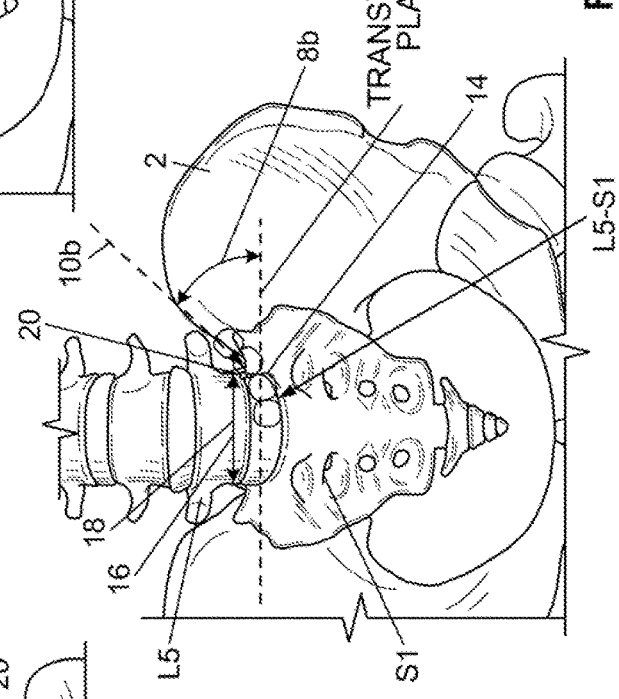
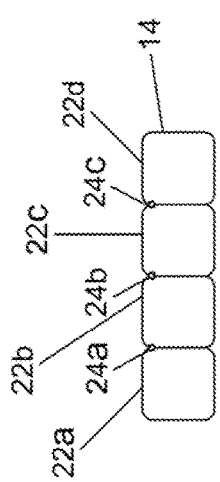
Fig. 5a NOT INVENTION
Fig. 5b
Fig. 5c
Fig. 5d

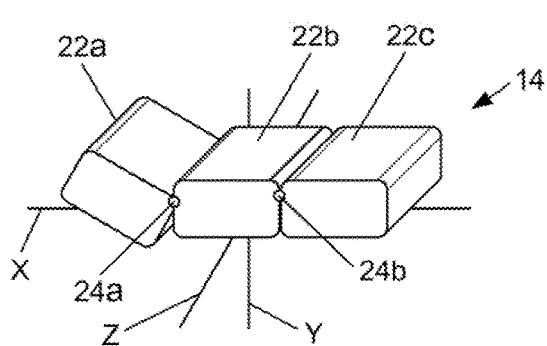 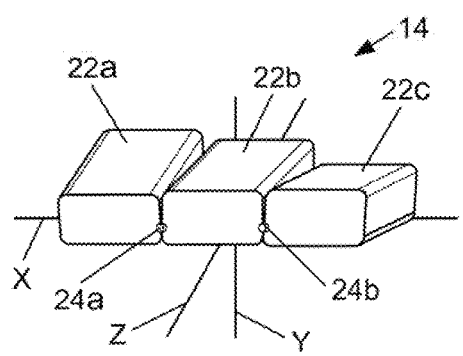
Fig. 9a    Fig. 9b
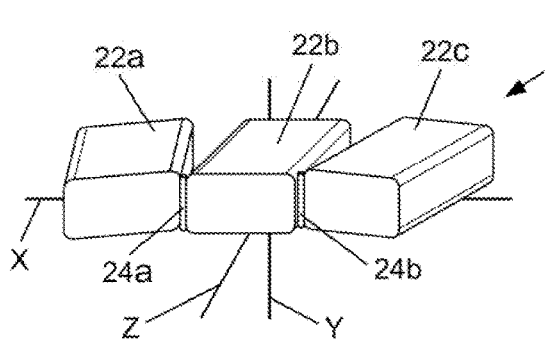 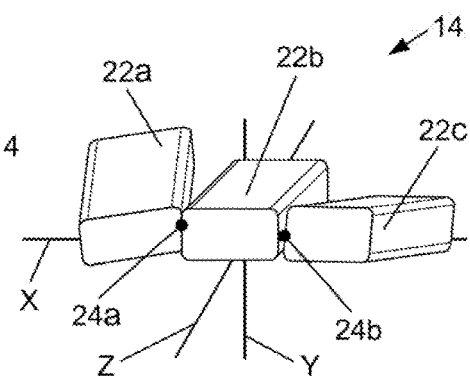
Fig. 9c    Fig. 9d

SUPPORT DEVICE AND METHOD FOR USE

CROSS-REFERENCE TO RELATED APPLICATIONS

This application is a continuation of U.S. patent application Ser. No. 13/773,100 filed Feb. 21, 2013, which is a continuation of PCT Application No. PCT/US2011/048992, filed Aug. 24, 2011, which claims priority to U.S. Provisional Patent Application No. 61/376,626, filed Aug. 24, 2010, and to U.S. Provisional Patent Application No. 61/526,630, filed Aug. 23, 2011, all of which are incorporated by reference herein in their entireties.

BACKGROUND OF THE INVENTION

1. Field of the Invention

A device, such as a flexible spinal fusion cage, which can articulate (bend) in such a way that it will be able to be implanted from a lateral approach into L4-L5 and L5-S1 is disclosed.

2. Description of the Related Art

Typical lateral approach fusion implants (e.g., Discover XLIF, by NuVasive, Inc., San Diego, Calif.; and the Direct Lateral Interbody Fusion (DLIF) by Medtronic, Inc., Minneapolis, Minn.) are not able to implant their fusion cages for two reasons.

First, boney obstacles can impair access. FIGS. 1a and 1b illustrate the pelvis and lower spine including the Ilium 2, sacrum S1, and lower lumbar vertebrae L3, L4 and L5. FIGS. 1a and 1b show the challenge of gaining lateral access to the L4-L5 and the L5-S1 intervertebral spaces. The position of the Ilium 2 obstructs the direct lateral access pathway.

FIG. 2 illustrates windows 4a and 4b or channels which some doctors create during implantation. The windows 4a and 4b are created through the Ilium to gain direct line of site access to the L4-L5 and L5-S1 intervertebral spaces, respectively. This is a highly invasive approach, creates significant tissue damage, particularly to the Ilium and surrounding soft tissue, and requires significant surgical skill.

Second, the steep approach angle (8a for the L4-L5 intervertebral space and 8b for the L5-S1 intervertebral space), as measured from a transverse plane along the approach path (10a for the L4-L5 intervertebral space and 10b for the L5-S1 intervertebral space) of a tissue retractor relative to the location of the fusion site, can cause problems, as illustrated in FIGS. 3 and 4. The approach paths 10a and 10b pass through the skin surface 12. The tissue retractor used in lateral fusion surgery provides line of site access to the disk space requiring a fusion cage insertion. The tissue retractor holds tissue out of the way of the procedure. The tissue retractor is also used to create a working channel to pass tools through, protect neural tissue, and anchor to the superior and inferior vertebral bodies relative the disk space requiring fusion. The volume within the pelvis and inferior to the dashed demarcation line 6 along a transverse plane is very hard if not impossible to reach with a direct lateral approach due to the Ilium. Even if the retractors are tilted as shown by the demarcation line 6, the ability to insert an implant that is the length of the end plates of the L4 or L5 vertebral bodies would be very difficult due to obstruction of the Ilium among other factors.

Furthermore, with the retractor positioned along the approach path 10a or 10b plane and angled direction, the angle formed between the retractor and the vertebral body end plates would make inserting a monolithic, inflexible fusion cage 14 or implant into the L5-S1 intervertebral space difficult if not virtually impossible due to obstruction of the surrounding hard and soft tissue, as illustrated by FIG. 5a. A typical lateral fusion cage or implant width 16 is the width of the end plate 18 along the adjacent disk. The implant 14 can not turn the corner at the pivot point 20 at the lateral and/or anterior edge of the L5-S1 intervertebral space.

SUMMARY OF THE INVENTION

Support or fixation devices and methods for access, controlling (e.g., steering or rotating, and driving or translating) implants, and modifying the configuration of implants are disclosed. The device can be an implantable fixation device, such as a flexible and/or articulatable fusion cage. The device can articulate and/or bend so the device can make the turn around the L5-S1 intervertebral space. The implant can flex and/or articulate. For example, the implant can have hinges and/or be flexible (e.g., have significantly elastic structural components).

Articulation tools are disclosed that can be used to implant the device. The articulation tools can articulate the device and/or allow the device to articulate. For example, the connection between the articulation tool and the implant can bend, flex, steer, or combinations thereof. The articulation tools can be used to debride or clear out the disk space.

An oblique curved access tool or device can be used. The device can be delivered to the intervertebral space along an oblique approach path, not perpendicular to the spine. The oblique approach can provide an access path from lateral skin to the L5-S1 disk space, and can curve tangent to the Ilium. A large working channel through the soft tissue can be created. The oblique access tool can move soft tissue out of the way to create the working channel. The oblique approach can reduce the access-tool-to-disk-space approach angle.

A biological implant support device for providing orthopedic support is disclosed. The device can be articulatable or flexible. The device can have a first rigid section at a first terminal end of the device. The first rigid section can have a first top plate and a first bottom plate. The device can have a second rigid section having a second top plate and a second bottom plate. The first rigid section can be rotatably attached to the second rigid section. The top and bottom plates can be configured to interface with hard tissue.

A method for inserting a support device to a target site in a spine adjacent to a first vertebra is disclosed. The method can include creating a channel through a non-vertebral bone. The method can include inserting a first rigid section of the device through the channel and into the target site. The method can include inserting a second rigid section of the device through the channel. The method can include rotating the second rigid section of the implant with respect to the first rigid section. The first rigid section can be hingedly attached to the second rigid section. The method can include inserting the second rigid section of the implant into the target site.

Creating the channel can include drilling the tissue with a flexible drill. The non-vertebral bone can be the pelvis, such as the ilium and/or the sacrum.

A method for inserting an implant to a target site between a first vertebra and a second vertebra is disclosed. The method can include creating a first channel through the ilium. The method can include creating a second channel through the sacrum. The first channel can be aligned with the second channel. The method can include inserting a first rigid section of the implant through the first channel and the second channel into the target site. The method can include rotating a second rigid section of the implant with respect to the first rigid section, wherein the first rigid section is hingedly attached to the second rigid section. The method can include inserting the second rigid section of the implant into the target site. The second channel can pass through a port formed in vertebral endplate. The device can be inserted through the port in the vertebral endplate and articulate as the device is delivered into the target site.

BRIEF DESCRIPTION OF THE DRAWINGS

FIGS. 1a and 1b are anterior and lateral views, respectively, of the lower lumbar and sacral spine and pelvis with the Ilium shown in phantom lines in FIG. 1b.

FIG. 2 is a lateral view of the lower lumbar spine with windows cut through the Ilium.

FIG. 5a is an anterior close-up view of the lower spine and pelvis with an approach of a monolithic implant.

FIG. 5b illustrates a variation of the implantable device.

FIGS. 5c and 5d illustrate a variation of a method of delivering the device of FIG. 5b into the L5-S1 space.

FIGS. 9a through 9d illustrate variations of the device in various configurations. An x-axis, y-axis and z-axis are also shown for orientation with the x-axis disposed along the longitudinal axis of the device.

DETAILED DESCRIPTION

Figure 3:
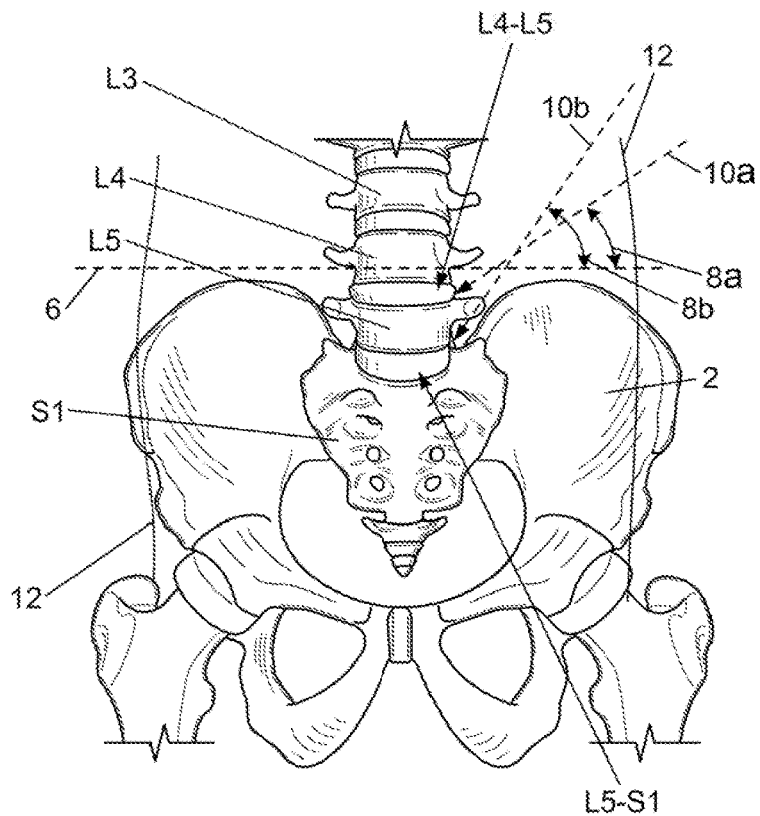
FIGS. 3 and 4 are anterior and lateral views, respectively, of the lower spine and pelvis along with approach paths into the intervertebral spaces.
Figure 4:
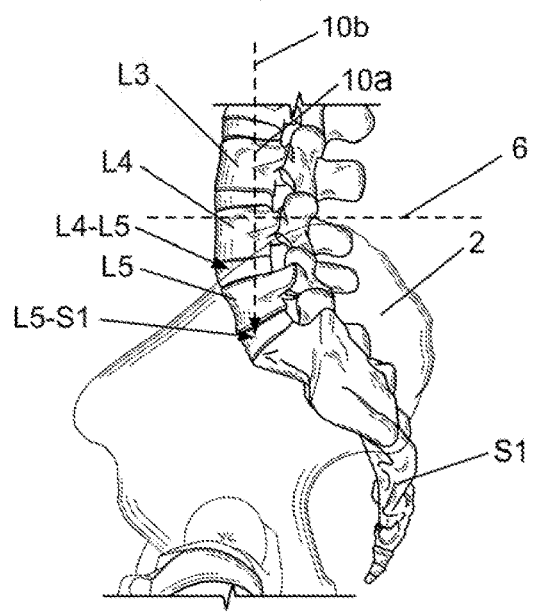

Support or fixation devices and methods for access, controlling (steering) implants, and modifying implants are disclosed. The support device disclosed herein can be used to treat one or more osseous structures in the body including the L4-L5 and L5-S1 region of the spine. The device can be used with known methods of accessing the vertebrae of the spine such as the L4-L5 and L5-S1 regions with posterior, anterior, or lateral approaches, or combinations thereof.

The device can be an implantable fixation device, such as a flexible fusion cage. The device can be delivered into an intervertebral space, for example, to provide structural support between the adjacent vertebrae. The device can fuse the vertebra adjacent to the specific intervertebral space. A discectomy can be performed at the target implant site before or during delivery of the implant.

FIGS. 5a through 5c illustrate that the device can be articulatable or flexible. The implantable device 10 can be used to support and/or fix structures between adjacent vertebrae, such as between the L4 and L5 vertebrae or between the L5 and S1 vertebrae. The implantable device 10 can be articulatable and/or flexible so as to navigate sharp anatomical turns, such as the L4-L5 or L5-S1 intervertebral space. The implantable device 10 can be rigidly lockable or can remain flexible or articulatable at all times. The implantable device 10 can be rigidly locked for example using a delivery tool, e.g., wires, sheaths, guides, or combinations thereof, for example, for additional stability. Such surgical delivery tools, alone or in combination, may add axial strength and stability before during or after pressing the implantable device 10 into the targeted intervertebral disc space.

FIG. 5b illustrates that the implantable device 14 can have first, second, third, and fourth segments 22a through 22d. Each of the segments 22a, 22b, 22c, and 22d can be attached to the adjacent segment at a flex point or articulatable hinge 24a, 24b, and 24c, respectively. The device 14 can articulate and/or bend at the hinges 24.

FIGS. 5c and 5d illustrate that the device 14 can be delivered into the L5-S1 intervertebral space. The device 14 can make the turn around the L5-S1 intervertebral space, such as at the pivot point 20, by articulating or flexing.

Figure 6:
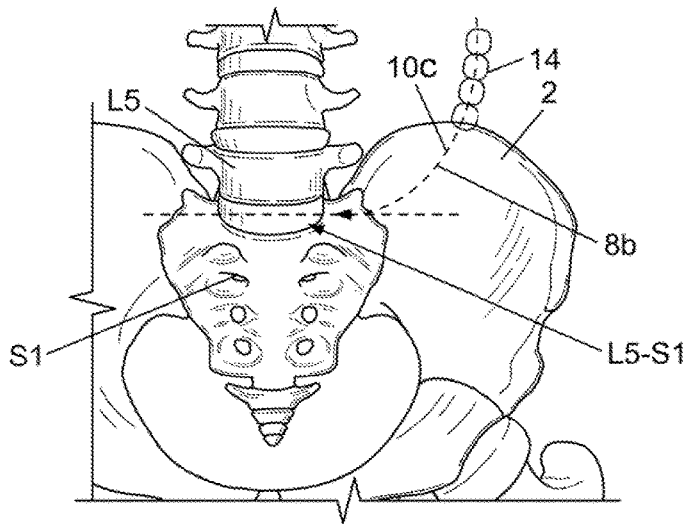
FIGS. 6 through 8 are anterior, perspective and lateral views, respectively, of a variation of the approach path for delivering the implant into the intervertebral space.
Figure 7:
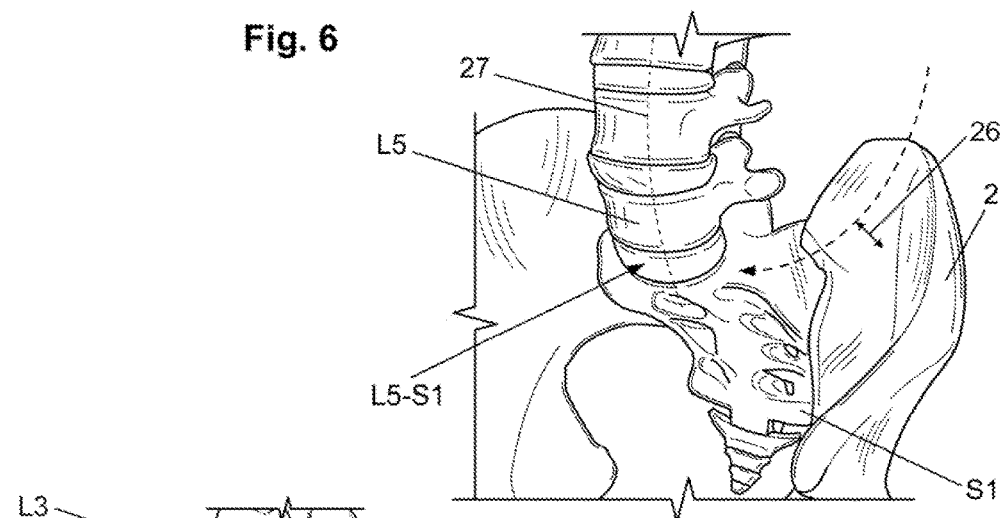
Figure 8:
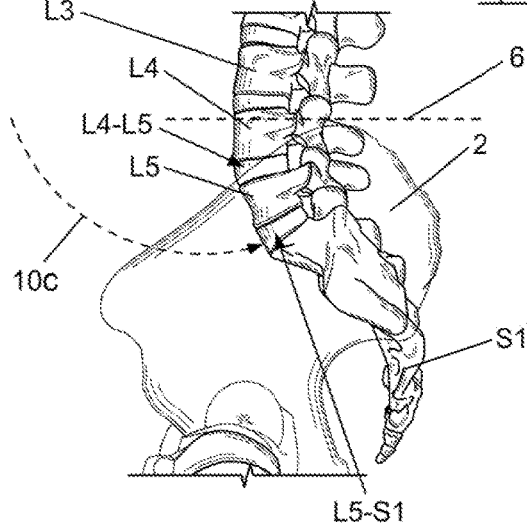

FIGS. 6 through 8 shows illustrate a curved implant pathway or approach path 10c. An articulation tool can be used to push (e.g., impact), pull, control or combinations thereof, the implant 14. The implant 14 can articulate and/or flex during delivery. The implant can have single or multiple hinges, a flexible shaft, laser slots (e.g., in a tube to act as hinges) or combinations thereof.

The approach path 10c can be tangential to the medial surface of the Ilium along a portion of the length of the approach path 10c. A portion of the length of the approach path 10c can be linear and a portion of the length of the approach path 10c can be curved. The entire approach path 10c can be linear or curved. A portion of the length of the approach path 10c can track (i.e., follow the same shape of) the medial surface of the Ilium. The approach path 10c can contact the medial surface of the Ilium 2. The approach path 10c can be non-perpendicular or perpendicular to the longitudinal axis 27 of the spine where the approach path 10c enters the intervertebral space L4-L5 or L5-S1.

The approach-Ilium gap 26 can be measured between the approach path 10c and the closest medial surface of the Ilium 2. The approach-Ilium gap 26 can be perpendicular to the approach path 10c and the Ilium 2, for example when the approach path 10c is tracking the medial surface of the Ilium 2. The approach-Ilium gap 26 can be from about 0 mm to about 15 mm along the length of the approach path 10c where the approach path is tracking the medial surface of the Ilium 2, more narrowly from about 0 mm to about 10 mm, yet more narrowly from about 2 mm to about 8 mm.

The approach path 10c can be curved in all three dimensions (e.g., in the transverse plane, sagittal plane and coronal plane), or any combination thereof and straight in the remaining dimensions.

FIG. 9a through 9d illustrate that variations of hinges 24a and 24b between the segments 22a, 22b and 22c can allow the implant 14 to articulate. The implant 14 can have controlled angulation or articulation (i.e., with discrete, defined built-in stopping points or stops) or free angulation or articulation (i.e., with no stops).

FIG. 9a illustrates that the hinges 24a and 24b can be oriented in parallel with the z-axis. The hinges can have a single degree of rotational freedom. The segments 24, 24b and 24c can articulate by rotating about the z-axis with respect to each other. The hinges 24a and 24b can be near the top (as shown), near the bottom, in the middle with respect to the y-axis, or combinations thereof of the device 14.

FIG. 9b illustrates that the hinges 24a and 24b can be oriented in parallel with the x-axis. The segments 24, 24b and 24c can articulate by rotating about the x-axis with respect to each other. The hinges 24a and 24b can be near the front (as shown), near the rear, in the middle with respect to the z-axis, or combinations thereof of the device 14.

FIG. 9c illustrates that the hinges 24a and 24b can be oriented in parallel with the y-axis. The segments 24, 24b and 24c can articulate by rotating, about the y-axis with respect to each other. The hinges 24a and 24b can be near the front (as shown), near the rear, in the middle with respect to the z-axis, or combinations thereof of the device 14.

FIG. 9d illustrates that the hinges 24a and 24b can be ball-in-socket hinges allowing three rotational degrees of freedom, or a combination of the three hinges described in FIGS. 9a through 9c, allowing two or three degrees of freedom. The segments 24, 24h and 24c can articulate by rotating about the x-axis, and/or y-axis, and/or z-axis with respect to each other. The hinges 24a and 24b can be near the front (as shown), near the rear, in the middle with respect to the z-axis, near the top, near the bottom, in the middle with respect to the y-axis (as shown), or combinations thereof of the device 14.

The first hinge 24a can be located in a different location and/or with a different than the second hinge 24b. For example, the first hinge 24a can be oriented in parallel with the z-axis, allow rotation about the z-axis and be located near the top of the device 14, and the second hinge 24b can be oriented in parallel with the x-axis, allow rotation about the x-axis, and be located near the middle of the device 14 with respect to the z-axis.

Figure 10A:
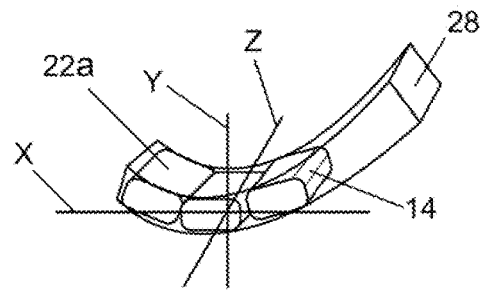
FIGS. 10a and 10b illustrate various configurations of a variation of the device in a steering tube with the tube shown as see-through for illustrative purposes.
Figure 10B:
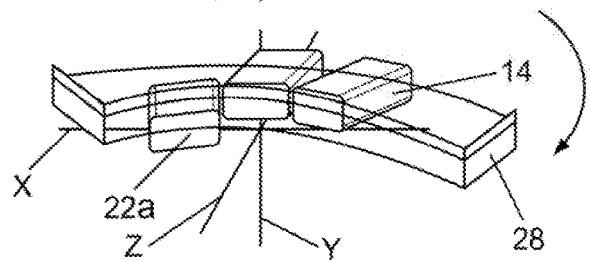

FIGS. 10a and 10b illustrate that the device 14 can have an outer steering sheath or tube 28. The device 14 can be fixed to the steering tube 28 or can slide along the steering tube 28. The steering tube 28 can be articulatable and/or flexible, as shown by the arrow in FIG. 10b and the various configurations of the tube 28 between FIGS. 10a and 10b. The articulation or flexion of the steering tube 28 can be controlled, for example by delivering controlled tension to tensile control wires in the walls of the steering tube 28.

The steering tube 28 can be positioned at the target deployment site. For example, the steering tube 28 can be placed in the intervertebral space and can remain in the intervertebral space post-surgery, or the steering tube 28 can be removed from the intervertebral space and the device 14 can be deployed from the tube 28 and the device 14 can be left in the intervertebral space.

Also for example, the distal end of the steering tube 28 can be positioned at the entrance to the intervertebral space and/or rested on the inferior and/or superior vertebral body end plate adjacent to the target intervertebral space. The device 14 can then be pushed (e.g., by a plunger) out of the steering tube and into the intervertebral space. The steering tube 28 does not have to, but can, enter the intervertebral space.

Figure 10C:
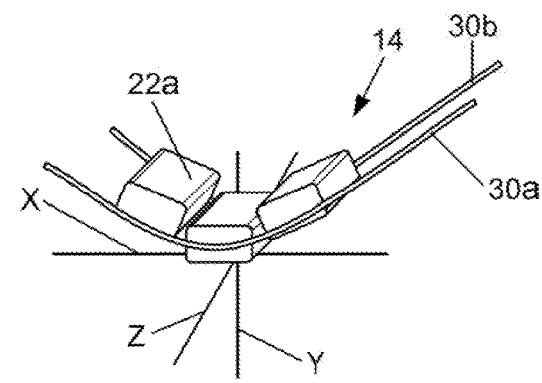
FIGS. 10c through 10e illustrate various configurations of a variation of the device on steering rails attached to the lateral outside of the device.
Figure 10D:
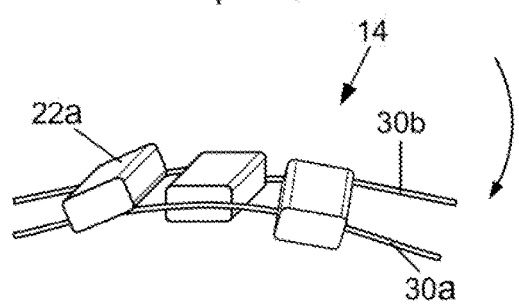
Figure 10E:
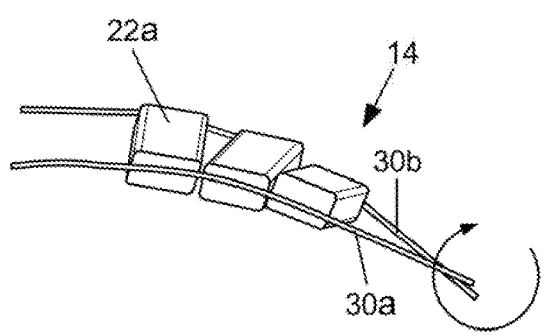

FIGS. 10c through 10d illustrate that the device 14 can have one or more exterior steering rails, tracks or wires 30a and 30b, such as guidewires. The rails 30a and 30b can slidably or fixedly and releasably engage the external surface of the segments 22 of the device 14. For example, the rails can pass through slots, guides, collars, cuffs or combinations thereof on the exterior of the segments 22. The slots, guides, collars, cuffs or combinations thereof, and/or the rails 30a and 30b can be coated or covered with a low-friction (e.g., PTFE) or high-friction (e.g., knurled or toothed surface texturing) material or surface treatment or texture, including any of the materials listed herein. The steering rails 30a and 30b can be steered or manipulated by applying a tensile force to tensile cables within the rails, as shown by the arrows in FIGS. 10d and 10e, and the flexing from FIGS. 10c to 10d. The rails 30a and 30b can be pre-formed to a specific shape and can be substituted for other rails 30a and 30b that can be pre-formed to a different shape to change the direction of delivery.

Figure 11A:
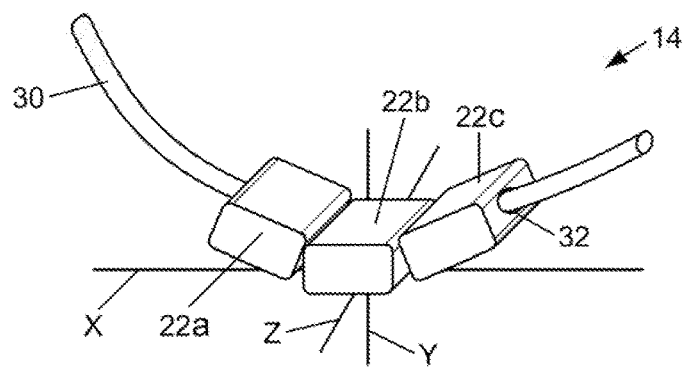
FIGS. 11a through 11c illustrate various configurations of a variation of the device on a steering rail attached to the inside of the device.
Figure 11B:
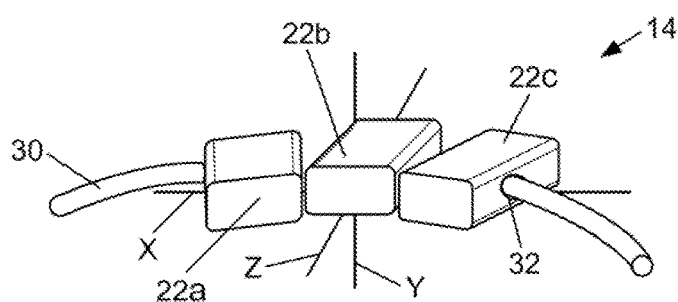
Figure 11C:
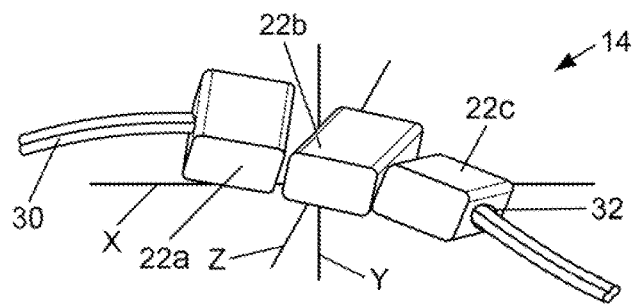

FIGS. 11a through 11c illustrates that the device 14 can have one or more interior steering rails, guide, tracks or wires 30, such as guidewires. The rails 30 can be positioned through the center or interior of one or more segments 22 of the device 14. The rail 20 can slidably or fixedly and releasably engage an internal surface, such as through a longitudinal guide port or channel 32, of the segments 22 of the device 14. For example, ports or channels can extend longitudinally through the segments 22 of the device 14. The channels, and/or the rail 30 can be coated, covered or collared, such as with a low-friction (e.g., PTFE) or high-friction (e.g., knurled or toothed surface texturing) material or surface treatment or texture, including any of the materials listed herein. The steering rail 30 can be steered or manipulated by applying a tensile force to tensile cables within the rail 30, as shown by the flexing from FIGS. 11a to 11c. The rail 30 can be pre-formed to a specific shape and can be substituted for one or more other rails 30 that can be pre-formed to a different shape to change the direction of delivery.

The distal ends of the internal and/or external steering rail or rails 30 can be positioned at the target deployment site. For example, the steering rails 30 can be placed in the intervertebral space and can remain in the intervertebral space post-surgery, or the steering rails 30 can be removed from the intervertebral space and the device 14 can be deployed from the rails 30 and the device 14 can be left in the intervertebral space.

Also for example, the distal end of the steering rails 30 can be positioned at the entrance to the intervertebral space and/or rested on the inferior and/or superior vertebral body end plate adjacent to the target intervertebral space. The device 14 can then be pushed (e.g., by a plunger) out of the steering rails 30 and into the intervertebral space. The steering rails 30 do not have to, but can, enter the intervertebral space.

Figure 12A:
FIGS. 12a through 12f are cross-sections of various steering rails, or along the length of the same steering rail.
Figure 12B:
Figure 12C:
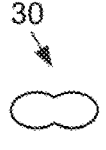
Figure 12D:
Figure 12E:
Figure 12F:

FIGS. 12a through 12f illustrate cross-sections of various rails 30, or at various lengths along the same rail 30. FIG. 12a illustrates that the cross-section of the steering rail 30 can be circular. FIG. 12b illustrates that the cross-section of the steering rail 30 can be oval. FIG. 12c illustrates that the cross-section of the steering rail 30 can be multi-ovular (i.e., having a union of two or more ovals with the same major axis). FIG. 12d illustrates that the cross-section of the steering rail 30 can be the union of rectangles intersecting at right (or another) angle, such as a plus-sign. FIG. 12e illustrates that the cross-section of the steering rail 30 can be hexagonal. FIG. 12f illustrates that the cross-section of the steering, rail 30 can be rectangular or square with sharp or rounded (chamfered) edges. The cross-section of the steering rail 30 can be triangular, pentagonal, heptagonal, or octagonal. The steering rail 30, whether internal or external to the device 14, can deliver torque around the longitudinal and/or transverse axes of the device. The steering rail 30 can have various cross sections at various lengths along the rail 30. The steering rail 30 can guide, pitch, yaw and roll the device 14 into a desired orientation or indication. The device 14 can be delivered with one or more internal and/or external rails 30 and/or a sheath 28 or neither.

Figure 13:
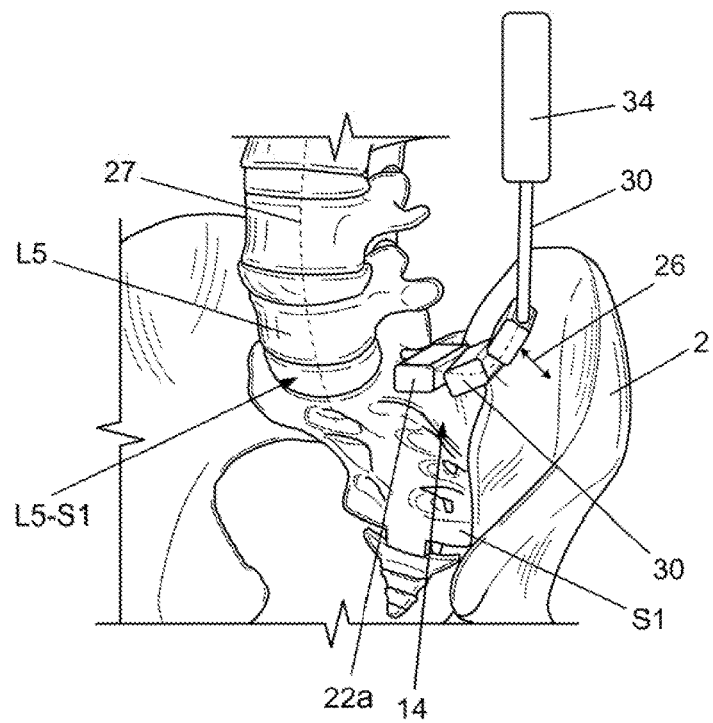
FIG. 13 illustrates a method for deploying the device into the L5-S1 intervertebral space.

FIG. 13 illustrates a device 14 that can be attached to a deployment tool having a controller handle 34 controllably attached to the internal steering rail 30. The internal steering rail 30 can pass through the device 14. The steering rail 30 can be fixedly attached to the device 14 during the delivery and articulation of the device 14. The device can be steered along or tracking the medial surface of the Ilium 2. The device 14 can then be positioned adjacent to the target site (e.g., the L5-S1 intervertebral space). The deployment tool can then release the device 14 from the steering rail 30 and push the device 14 into the target site.

Figure 14A:
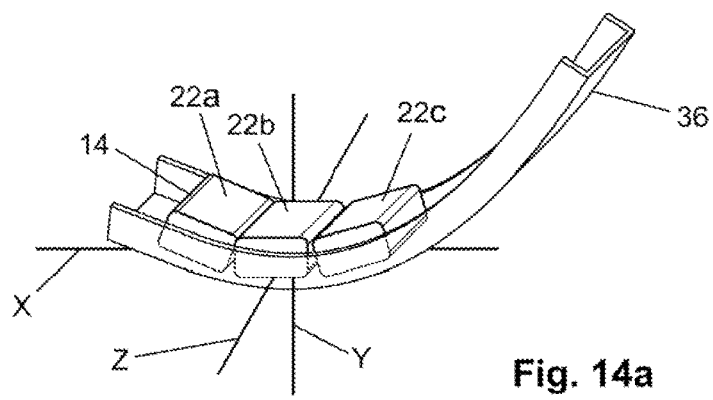
FIGS. 14a and 14b illustrate various configurations of a variation of the device in a steering slide.
Figure 14B:
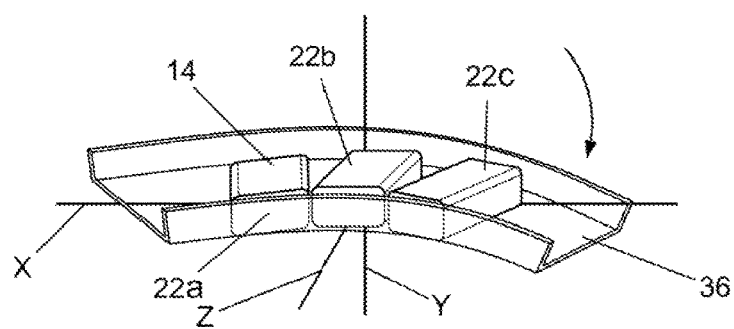

FIGS. 14a and 14b illustrate that the device 14 can be delivered by being pushed along a steering horn, boot, or slide 36. The slide 36 can be similar to the steering tube 28, except that at least one wall of the slide 36 can be missing or open (e.g., the top wall is not present in the variation of the slide shown) compared with the steering tube 28. The missing wall can be completely open or replaced by one or more steering rails 30. The slide 36 can be used similar to the steering rails 30 and/or steering tube 28. The slide 36 can be steered, flexed or articulated by applying a tensile force to tensile cables within the rails, as shown by the arrow in FIG. 14b, and the flexing from FIGS. 14a to 14b.

Figure 15A:
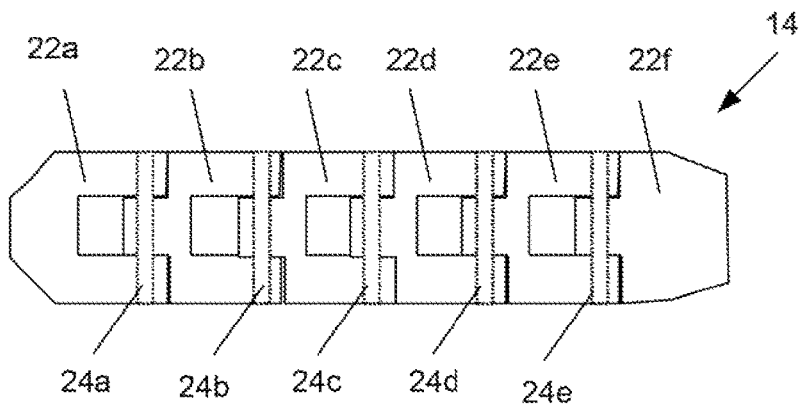
FIGS. 15a and 15b are top and side views of a variation of the device with parallel hinges.
Figure 15B:
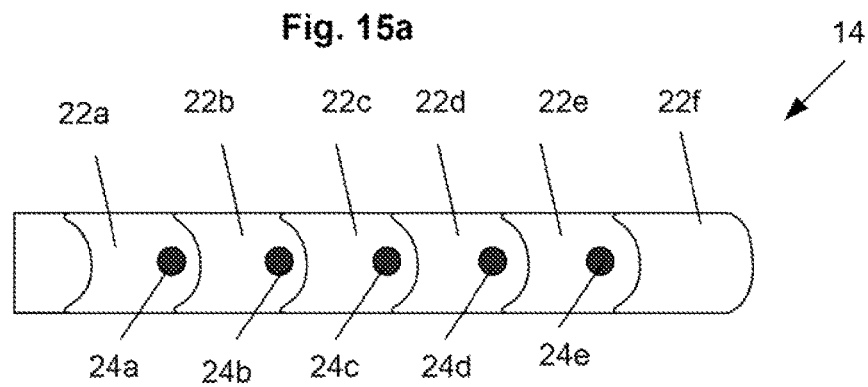

FIGS. 15a and 15b illustrate that the device 14 can have six segments 22a through 22f and five hinges 24a through 24e. The segments 22 can be attached to adjacent segments 22 by one or more hinges, tension or steering rails or wires, screws, pins, or combinations thereof. The hinges 24 can be pins. The segments 22 can be chained together. The segments 22 can be identical to each other except for the distal-most segment 22a and the proximal-most segment 22f. The segments 22 or links can be box-shaped. The hinges 24, such as the pins, can be parallel to all or some of the other hinges 24.

Figure 16:
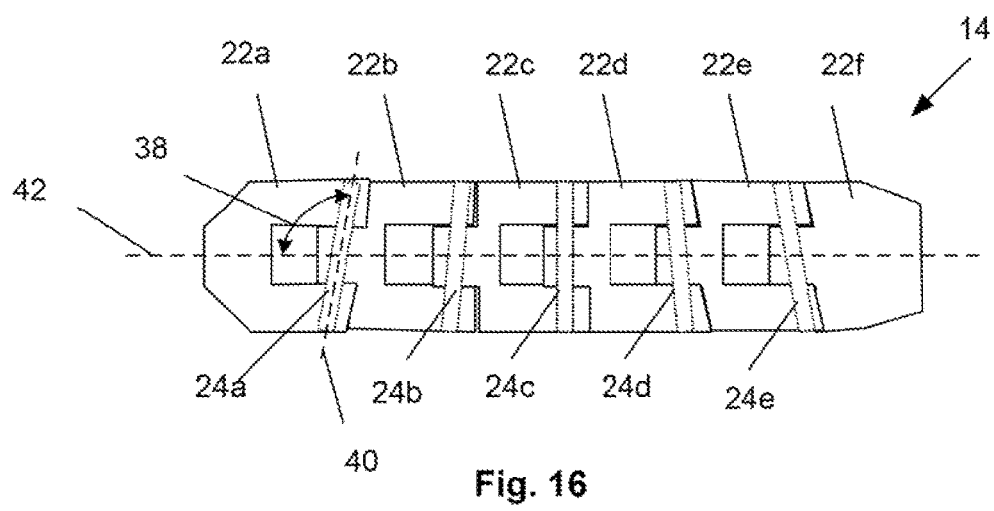
FIG. 16 is a top view of a variation of the device with non-parallel hinges.

FIG. 16 illustrates that the hinges 24 can be at acute angles to all or some of the hinges 24. The hinges 24 can be at hinge angles 38 with respect to each other. The hinge angle 38 can be measured between the hinge longitudinal axis 40 and the device longitudinal axis 42. The hinge angles 38 can be from about 80° to about 150°, more narrowly from about 90° to about 135°, yet more narrowly from about 95° to about 110°.

The device 14 can be translated and/or rotated by a handle 34 that can be removably attached to the device 14. The handle 34 can be screwed and/or snapped directly into the proximal end of the device 14, such as into the proximal-most segment 22. The handle 34 can compress, such as by grabbing or pinching, the proximal end of the device 14. The handle 34 can be a pusher, plunger, ram, or combinations thereof. The handle 34 and/or remainder of the deployment tool can be rigid and/or flexible or articulatable. For example, hinged similar to the device 14.

The segments 22 are not necessarily connected to each other by hinges. The segments 22 can be delivered to the target site individually, or as an unattached line of segments 22.

The device 14 can be cylindrical and flexible. The implantable device 14 can be fully flexible all the time. The device 14 can be mechanically stabilized by the deployment tool, steering wires, sheaths, tubes and guides. For example, the tools, wires, sheaths, tubes and guides can provide column stability to press the device 14 into the target site (e.g., intervertebral disc space).

The device 14 can flexible, and then locked with a tension or steering wire to stop rotational motion of the hinges once the device is delivered to and oriented within the target site. The tension wire could be tightened, for example by being tensioned by a nut to create higher friction in each hinge 24.

FIGS. 17a through 17f illustrate that the device 14 can have a living hinge 44. The living hinge 44 is a length of decreased rigidity and increased flexing within the body of the device 14. The living hinge 44 can be formed around slots and continuous segments of otherwise tough, durable material. The living hinge 44 can be defined be narrowing or thinning in the body of the device 14, such that the narrowing is sufficient to provide flexibility under reasonable torque. For example, the thickness of the unitary body of the device 14 at the living hinge 44 can be narrowed by more than about 85%, or more than about 90%, or more than about 95%, or more than about 97%, or more than about 98.5%. The living hinge 44 can have one or more repeated thinnings along the length of the device 14, as shown in FIGS. 17a through 17f.

Figure 17A:
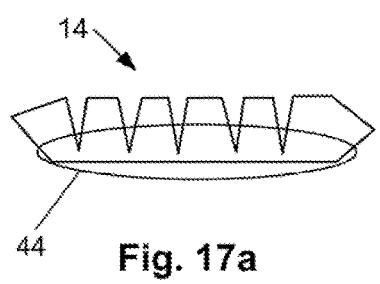
FIGS. 17a through 17f are side views of variations of the device.
Figure 17B:
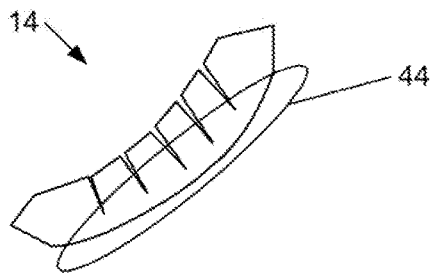

FIGS. 17a and 17b illustrate that the device 14 bends at the living hinge 44. The living hinges 44 can be made to control the bend and direction of the device 14. The outer surface of the device 14 along the living hinge 44 can be smooth, for example providing low-friction surface for sliding over bone.

Figure 17C:
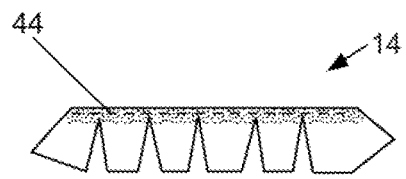
Figure 17D:
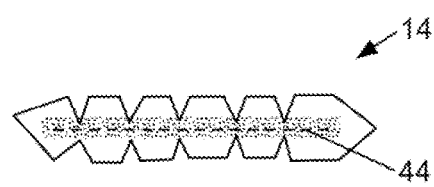
Figure 17E:
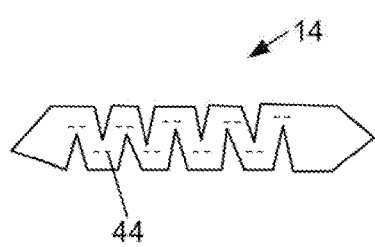
Figure 17F:
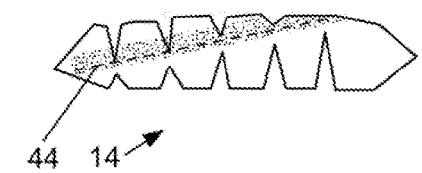

FIGS. 17a and 17b illustrate that the living hinge 44 can be along the bottom of the implant device 14. FIG. 17c illustrates that the living hinge 44 can be along the top of the device 14. FIG. 17d illustrates that the living hinge 44 can be through the middle or central axis of the device 14. FIG. 17e illustrates that the living hinge 44 is discontinuous and on opposite sides of the center of the device 44. FIG. 17f illustrates that the living hinge 44 is at an angle with respect to the longitudinal axis of the device 14, starting near the bottom of the device 14 and ending near the top of the device 14.

Figure 18:
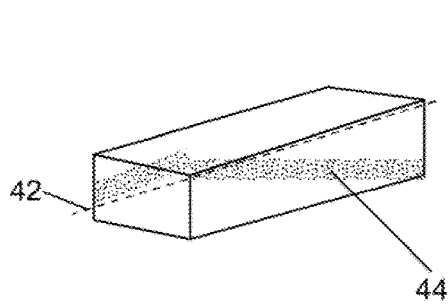
FIGS. 18 and 19 are perspective views showing the orientation of variations of living hinges within devices.

FIG. 18 illustrates that the living hinge 42 can be at a non-zero angle to the central longitudinal axis 42 of the device 14. A first length of the living hinge 42 can be at a non-zero angle to a second length of the living hinge 44.

Figure 19:
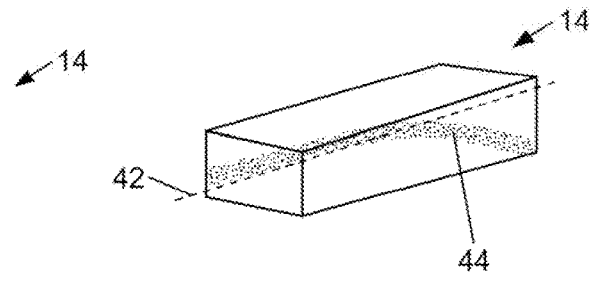

FIG. 19 illustrates that the living hinge 44 can be curved. The living hinge 44 can curve around the central longitudinal axis 42 of the device 14.

Figure 20A:
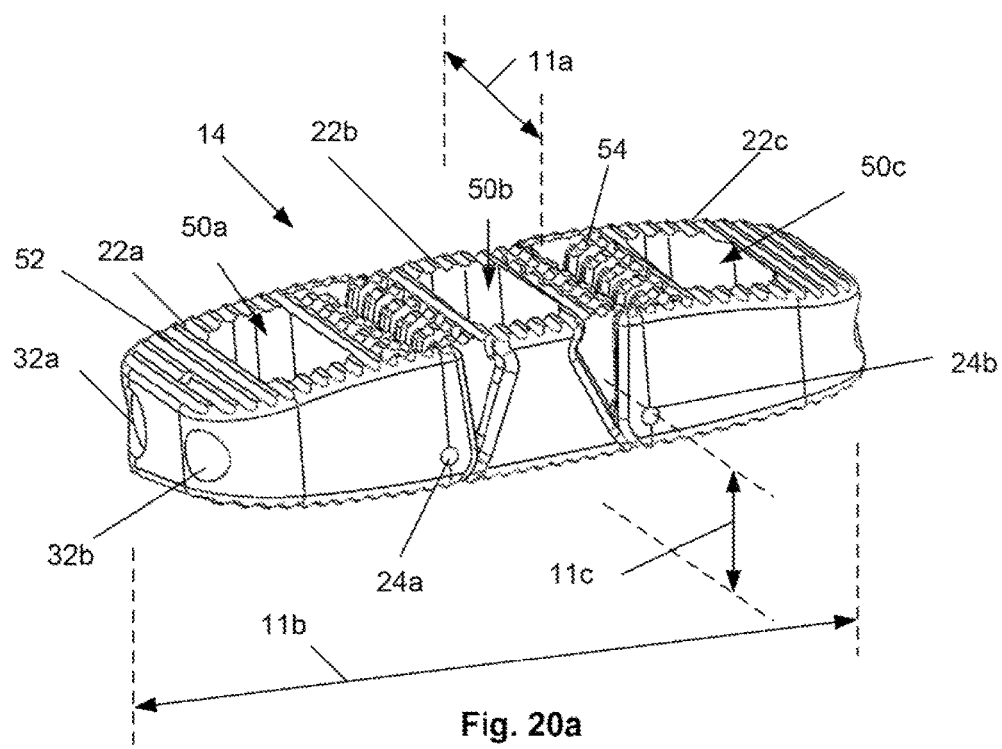
FIGS. 20a through 20c are perspective, top and front views, respectively, of a variation of the device in a straight or flat configuration.
Figure 20B:
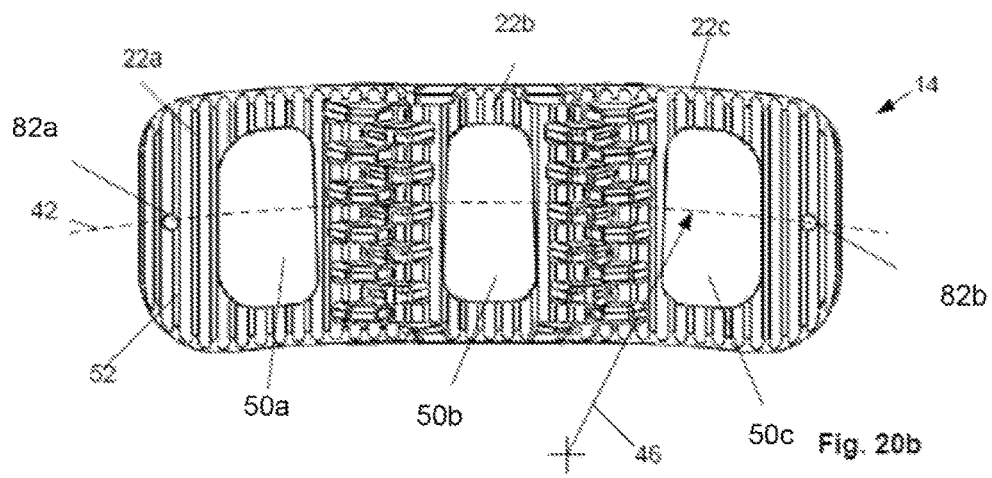
Figure 20C:
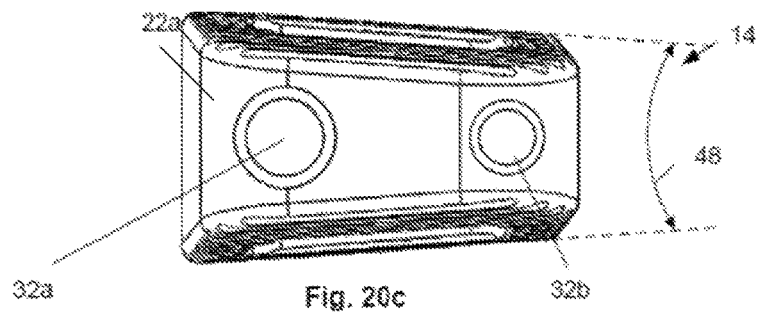

FIGS. 20a through 20c illustrate that the device can have three segments 22a, 22b and 22c connected by two hinges 24a and 24b. The device longitudinal axis 42 can be straight or can have a longitudinal radius of curvature 46. The longitudinal radius of curvature 46 can be from about 3 cm to about 100 cm, more narrowly from about 5 cm to about 20 cm, yet more narrowly from about 7 cm to about 15 cm, for example about 15 cm, also for example about 10 cm.

The support device 14 can have a support device width 11a, a support device length 11b and a support device height 11c. The support device width 11a can be from about 10 mm to 30 mm, or more narrowly 16 mm to about 18 mm. The support device length 11b can be from about 30 mm to 60 mm, or more narrowly from 45 mm to about 55 mm. The support device height 11c can be from about 1 mm to 30 mm, or more narrowly from 8 mm to about 16 mm.

The device 14 can have an anterior taper or lordosis angle 48. The taper angle 48 can be measured between the plane of the top surface and the plane of the bottom surface of the device 14. The taper angle 48 can be from about 0° (i.e., parallel top and bottom planes) to about 45°, more narrowly from about 2° to about 20°, yet more narrowly from about 0° to about 12°, yet more narrowly from about 4° to about 10°, yet more narrowly from about 4° to about 8°, for example from about 0°, also for example about 6°.

The first, second, and third links or segments 22a, 22b and 22c of the flexible implantable device 14 may be separate or connected. One or more of the segments 22 can be rigid and/or flexible. One or more of the segments 22 can have through-ports or segment ports 50, such as first, second and third segment ports 50a, 50b and 50c, through the first, second and third segments 22a, 22b, and 22c, respectively. The segment ports 50 can extend through part of all of the height of the respective segment 22 or the device 14 from the top to the bottom surface. One or more of the segment ports 50 can be partially or completely filled with a bone ingrowth matrix, bone morphogenic protein, therapeutic agents, any agent or material disclosed herein, or combinations thereof, for example for analgesic effect or to promote bone ingrowth.

The device 14 can have a surface coating or texturing on the top, and/or bottom, and/or side surfaces, such as lateral teeth 52, longitudinal or angled teeth, knurling, a coating or matrix to promote bone ingrowth, or combinations thereof.

The device 14 can have hinge teeth or knuckles 54. The hinge teeth 54 can slide by adjacent hinge teeth 54 to increase lateral stability during articulation and increase range of motion (e.g., a hinge tooth 54 on one segment 22 can slide into the gap between hinge teeth 54 on the adjacent segment 22 during articulation of the device 14).

One or more tension and/or steering wires can be inserted and/or tensioned through guide ports or channels 32a and 32b. The guide channels 32a and 32b can extend longitudinally through some or all of the segments 22.

The first segment 22a and the third segment 22c can have central vertical holes 82a and 82b, respectively. The central vertical holes 82 can be attached to a deployment device, screwed to the adjacent tissue (i.e., bone) after delivery, filled with a radiopaque material for visualization or therapeutic or other material listed herein, or combinations thereof.

Figure 21A:
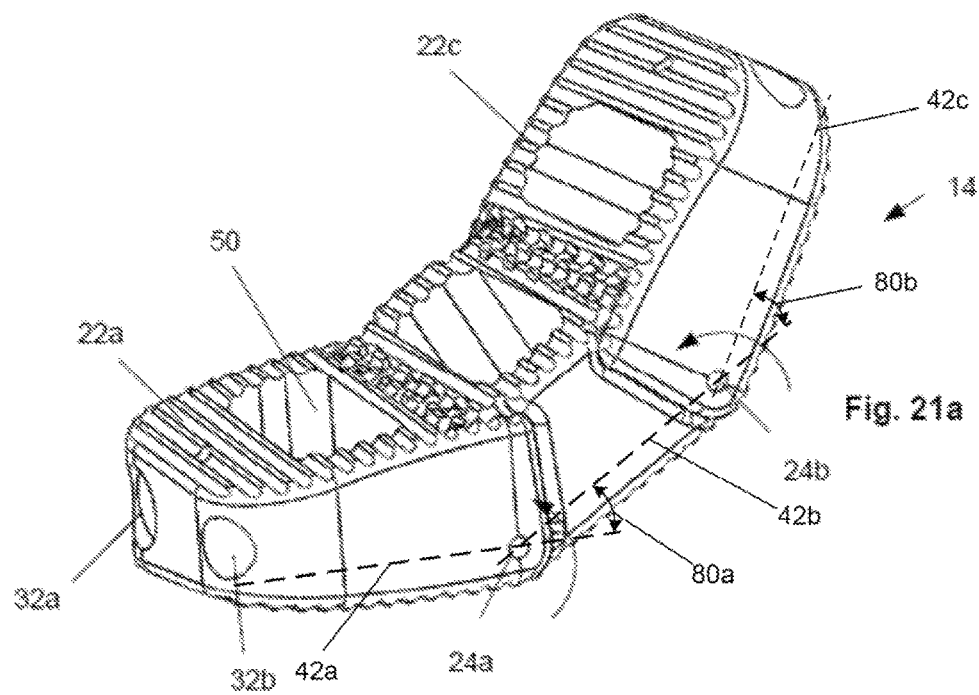
FIGS. 21a through 21c are perspective, top and front views, respectively, of the device of FIGS. 20a through 20c in an articulated configuration.
Figure 21B:
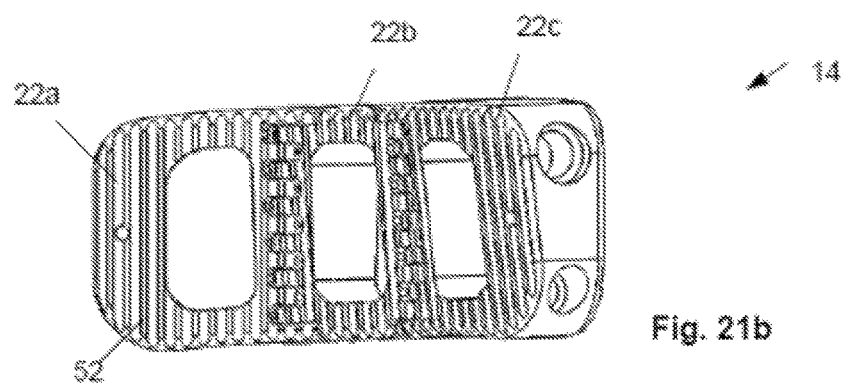
Figure 21C:
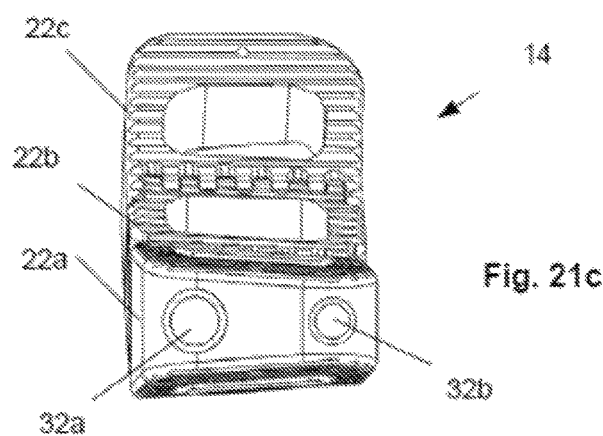

FIGS. 21a through 21c illustrate that device 14 can articulate. The segments 22 can rotate with respect to each other about the hinges 24, as shown by arrows.

The first segment 22a can have a first segment longitudinal axis 42a. The second segment 22b can have a second segment longitudinal axis 42b. The third segment 22c can have a third segment longitudinal axis 42c. The respective longitudinal axes can intersect at the adjoining, hinge pins 24. The first segment longitudinal axis 42a can form a first articulation angle 80a with the second segment longitudinal axis 42b. The second segment longitudinal axis 42b can form a second articulation angle 80b with the third segment longitudinal axis 42c. The first and second articulation angles 80a and 80b can be the same or different. When the device is in an articulated configuration, the first and/or second articulation angles 80a and/or 80b can be from about 0° to about 90°, more narrowly from about 3° to about 75°, yet more narrowly from about 5° to about 60°, yet more narrowly from about 15° to about 45°.

Figure 22A:
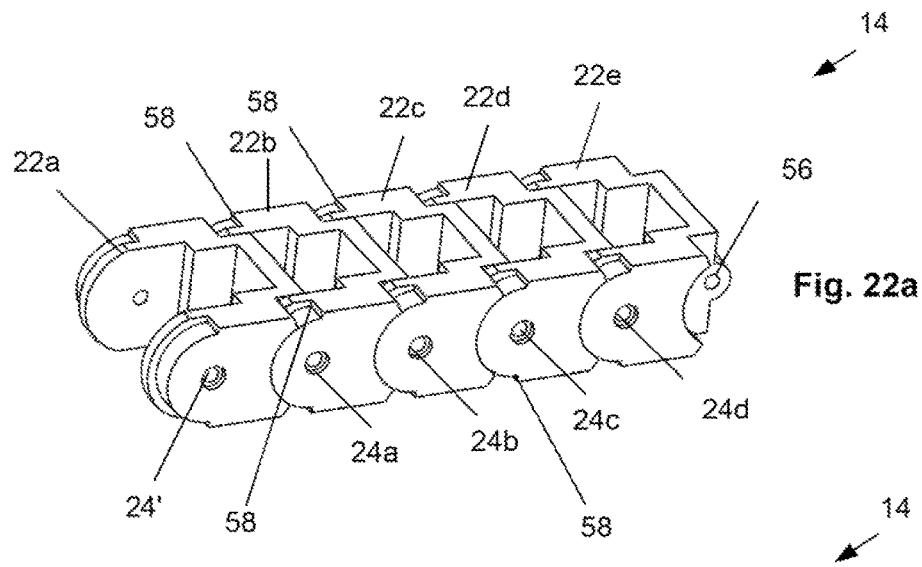
FIGS. 22a through 22c are perspective, top and front views, respectively, of a variation of the device in a straight or flat configuration.
Figure 22B:
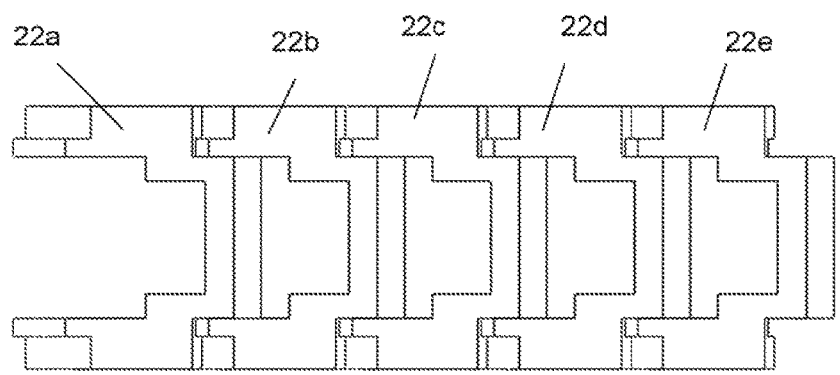
Figure 22C:
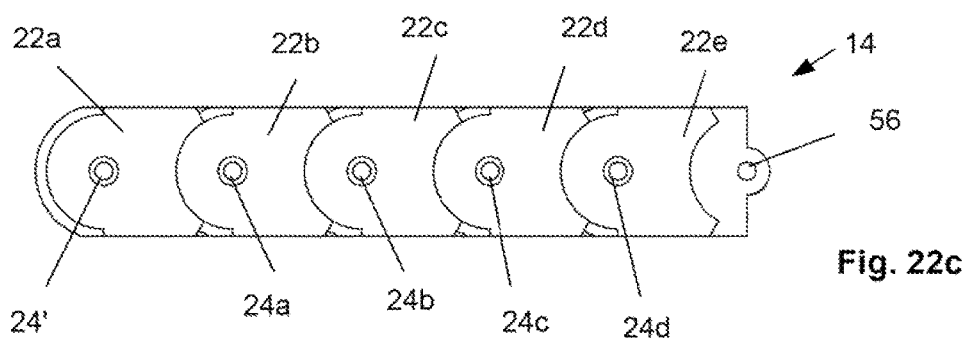

FIGS. 22a through 22c illustrate that some or all of the distal-most segments 22a through 22d can be identical. Segments 22 can be added or removed from the device 14, before during or after deployment to the target site, to increase or decrease the length of the device 14 to best fit the target site. The false hinge 24' can be a hinge component that is not attached to the other half of the hinge 24. The hinges 24 can snap together and apart. The articulation of each segment 22 can be limited by the interference fit of a rotational stop 58 on the top and bottom of the adjacent segment 22.

The device 14 can have a deployment tool interface, such as the lateral hole 56, for attaching to the deployment tool.

Figure 23A:
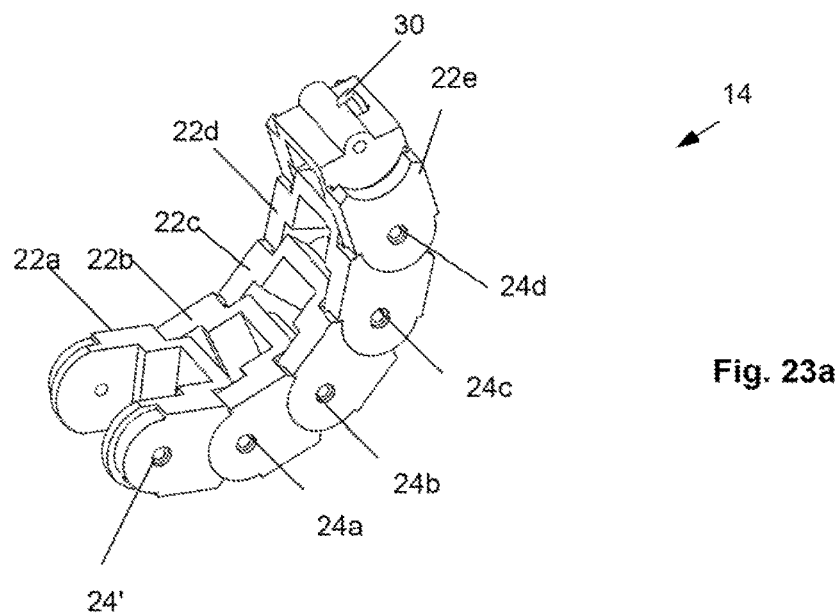
FIGS. 23a through 23c are perspective, top and front views, respectively, of the device of FIGS. 22a through 22c in an articulated configuration.
Figure 23B:
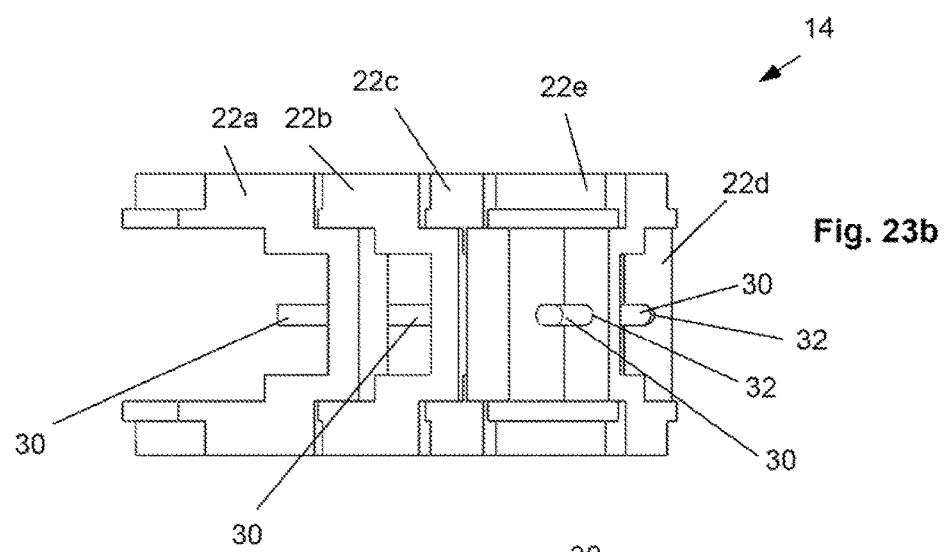
Figure 23C:
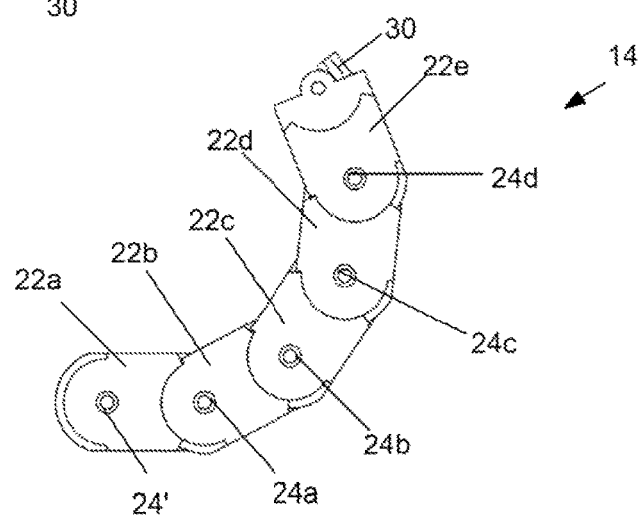

FIGS. 23a through 23c illustrate that a tensioning or steering wire or rail 30 can be deployed through the channels 32 on each segment. The wire 30 can then be tensioned to articulate and/or lock the device 14 in an articulated configuration.

PCT Application No. PCT/US 11/00974 filed 27 May 2011 which claims priority to U.S. Provisional App. No. 61/349,151 filed 27 May 2010 are both herein incorporated by reference in their entireties.

Any or all elements of the device and/or other devices or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CON-ICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET)/polyester (e.g., DACRON® from E. I. Du Pont de Nemours and Company, Wilmington, Del.), polypropylene, (PET), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyimide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), polylactic acid (PLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum and gold.

Any or all elements of the device and/or other devices or apparatuses described herein, can be, have, and/or be completely or partially coated with agents and/or a matrix a matrix for cell ingrowth or used with a fabric, for example a covering (not shown) that acts as a matrix for cell ingrowth. The matrix and/or fabric can be, for example, polyester (e.g., DACRON® from E. I. Du Pont de Nemours and Company, Wilmington, Del.), polypropylene, PTFE, ePTFE, nylon, extruded collagen, silicone or combinations thereof.

The device and/or elements of the device and/or other devices or apparatuses described herein and/or the fabric can be filled, coated, layered and/or otherwise made with and/or from cements, fillers, glues, and/or an agent delivery matrix known to one having ordinary skill in the art and/or a therapeutic and/or diagnostic agent. Any of these cements and/or fillers and/or glues can be osteogenic and osteoinductive growth factors.

Examples of such cements and/or fillers includes bone chips, demineralized bone matrix (DBM), calcium sulfate, coralline hydroxyapatite, biocoral, tricalcium phosphate, calcium phosphate, polymethyl methacrylate (PMMA), biodegradable ceramics, bioactive glasses, hyaluronic acid, lactoferrin, bone morphogenic proteins (BMPs) such as recombinant human bone morphogenetic proteins (rh-BMPs), other materials described herein, or combinations thereof.

The agents within these matrices can include any agent disclosed herein or combinations thereof, including radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin $E_2$ Synthesis in Abdominal Aortic Aneurysms, Circulation, Jul. 6, 1999, 48-54; Tambiah et al, Provocation of Experimental Aortic Inflammation Mediators and *Chlamydia Pneumoniae*, *Brit. J. Surgery* 88 (7), 935-940; Franklin et al, Uptake of Tetracycline by Aortic Aneurysm Wall and Its Effect on Inflammation and Proteolysis, *Brit. J. Surgery* 86 (6), 771-775; Xu et al, Sp1 Increases Expression of Cyclooxygenase-2 in Hypoxic Vascular Endothelium, *J. Biological Chemistry* 275 (32) 24583-24589; and Pyo et al, Targeted Gene Disruption of Matrix Metalloproteinase-9 (Gelatinase B) Suppresses Development of Experimental Abdominal Aortic Aneurysms, *J. Clinical Investigation* 105 (11), 1641-1649 which are all incorporated by reference in their entireties.

Methods of Use

Figure 24:
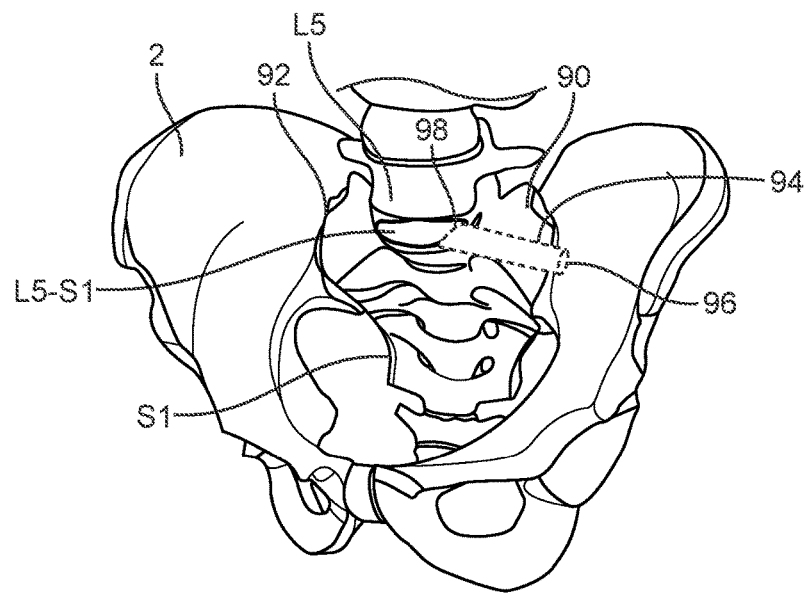
FIG. 24 illustrates the lower spine and pelvis.

FIG. 24 illustrates that a straight or curved transosseous delivery channel 94 can be drilled, chiseled, punched, or a combination thereof, through the iliac bone 2 and/or the sacral ala 90, for example passing through the sacroiliac joint 92. The transosseous delivery channel 94 have a first length or first channel through the iliac 2 and a second length or second channel through the sacrum S1. The first length of the transosseous delivery channel 94 can be aligned with the second length of the transosseous delivery channel 94, for example to form a substantially continuous channel. The transosseous delivery channel 94 can have a laterally-located channel entry port 96 laterally outside of the sacral ala 90 and/or iliac bone 2. The transosseous delivery channel 94 can have a channel exit port 98 adjacent to the L5-S1 intervertebral disc space. For example, the channel exit port 98 can be in the S1 endplate. The channel exit port 98 can be positioned so the circumference of the channel exit port 98 tangentially coincides with or is closely adjacent to (e.g., within about 2 cm, more narrowly within about 1 cm, more narrowly within about 5 mm, yet more narrowly within about 2 mm) with the edge of the S1 vertebral endplate 100.

The L5-S1 intervertebral space can be partially or completely void of soft tissue, as shown, for example from a discectomy performed before insertion of the support device 14. For example, the discectomy can be performed by the method and device shown in U.S. Provisional Patent Application No. 61/526,630 filed 23 Aug. 2011, which is incorporated by reference herein in its entirety.

Figure 25:
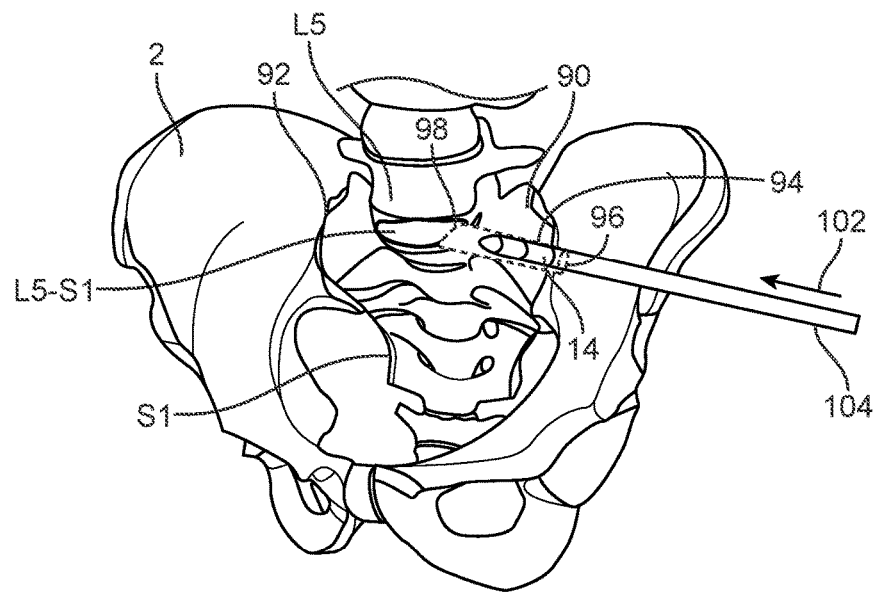
FIGS. 25 through 28 illustrate a variation of a method of delivering the device to a target site.

FIG. 25 illustrates that the support device 14 can be inserted, as shown by arrow 102, medially through the channel entry port 96 of the transosseous delivery channel 94. The device 14 can be removably and/or articulatably attached to a deployment tool shaft 104.

Figure 26:
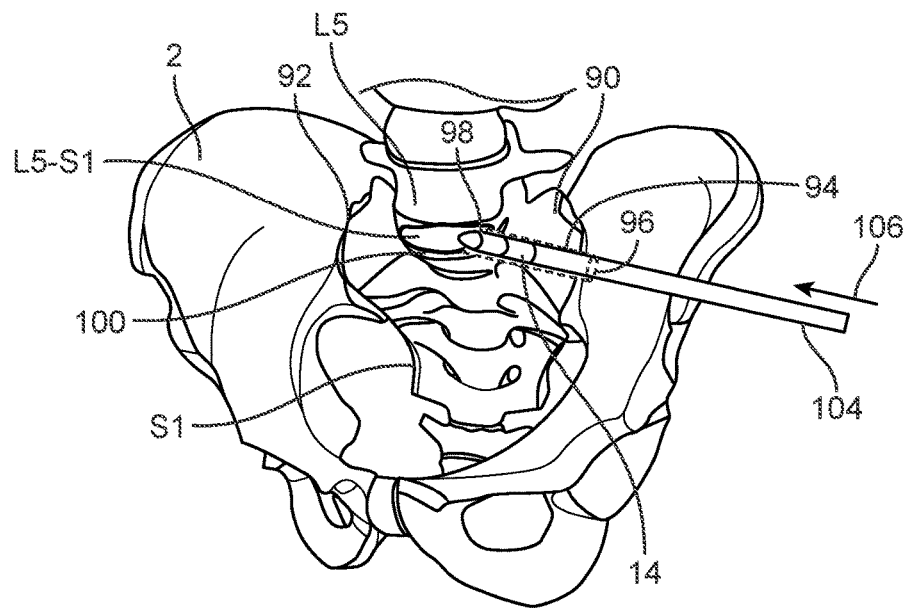

FIG. 26 illustrates that the shaft 104 can be further translated, as shown by arrow 106, into the transosseous delivery channel 94. The support device 14 can translate toward and into the L5-S1 intervertebral disc space. The distal tip of the support device 14 can enter the L5-51 intervertebral disc. The support device 14 can enter the target site of the L5-S1 intervertebral disc directly from the transosseous delivery channel 94 without passing through any soft tissue between the L5-S1 intervertebral disc and the iliac bone 2.

Figure 27:
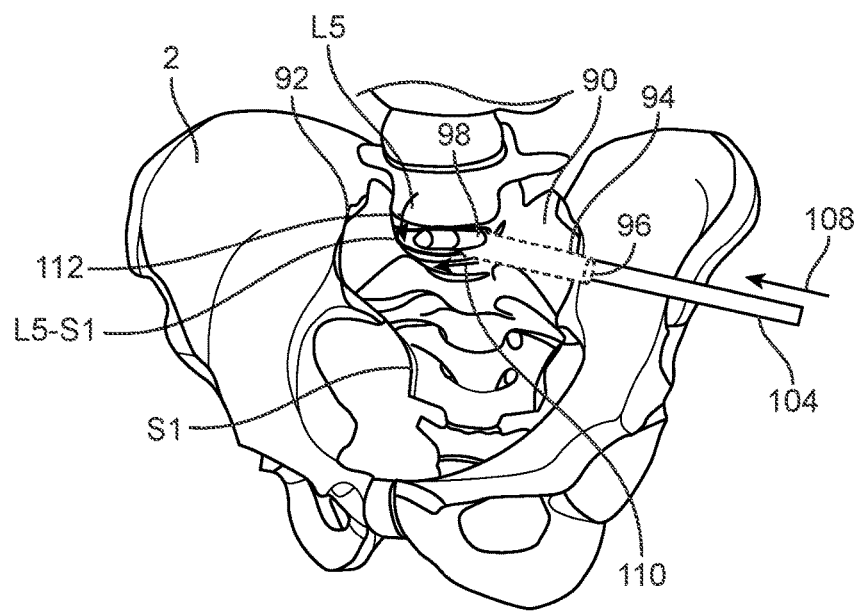

FIG. 27 illustrates that the shaft 104 can be further translated, as shown by arrow 108, medially through the transosseous delivery channel 94. The device 14 can translate, as shown by arrow 110, through the L5-S1 intervertebral disc space and the L5 and/or the S1 vertebra. The support device 14 can articulate, as shown by arrow 112. One or more of the hinges 24 can rotate, articulating the segments 22. The hinges 24 can be controllably rotatably locked and unlocked, for example, by controls on the handle of the deployment tool (of which the shaft 104 is a part).

The support device 14 can then be further translated, such as being pushed and/or vibrated (e.g., manually, ultrasonically), for example, medially and laterally, and/or superior and inferiorly, and/or anteriorly and posteriorly. The through ports and/or cavities and/or recesses 50 in the device 14 can be partially and/or completely filled bone morphogenic protein, therapeutic agents, other materials listed herein or combinations thereof. The support device 14 can deliver a cauterizing electrical energy from the deployment tool. The support device 14 and shaft 104 can have one or more longitudinal lumens that can be used to irrigate (e.g., with analgesic agents, saline, anesthetic agents, bone morphogenic proteins, visualization agents, other agents described herein, or combinations thereof) and/or aspirate (e.g., to remove irrigated material and/or debris) the target site (e.g., the L5-S1 intervertebral disc space).

Figure 28:
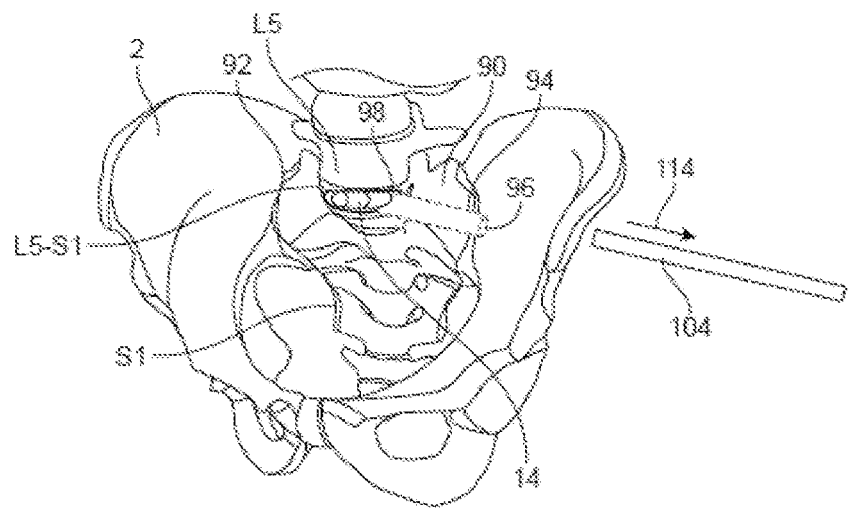

FIG. 28 illustrates that before, during or after the support device 14 is positioned in the L5-S1 intervertebral space, the shaft 104 can detach from the support device 14 and be translated laterally, as shown by arrow 114, from the L5-S1 intervertebral disc space and the transosseous delivery channel 94. The deployment tool shaft 104 can remove or reposition the support device 14, or leave the support device 14 in place in the L5-S1 space.

The method shown in FIGS. 25 through 28 can be repeated to deliver multiple support devices 14 to one or more intervertebral spaces. For example, one, two, three or more support devices 14 can be positioned in the L4-L5 intervertebral space and/or the L5-S1 intervertebral space. The one, two, three or more support devices 14 positioned in the L4-L5 and/or L5-S1 intervertebral spaces, can mechanically support the adjacent vertebrae and/or fix the adjacent vertebrae to each other. Bone ingrowth can occer through the through ports 50, for example fusing the support devices 14 to the respective surrounding vertebrae.

Figure 29:
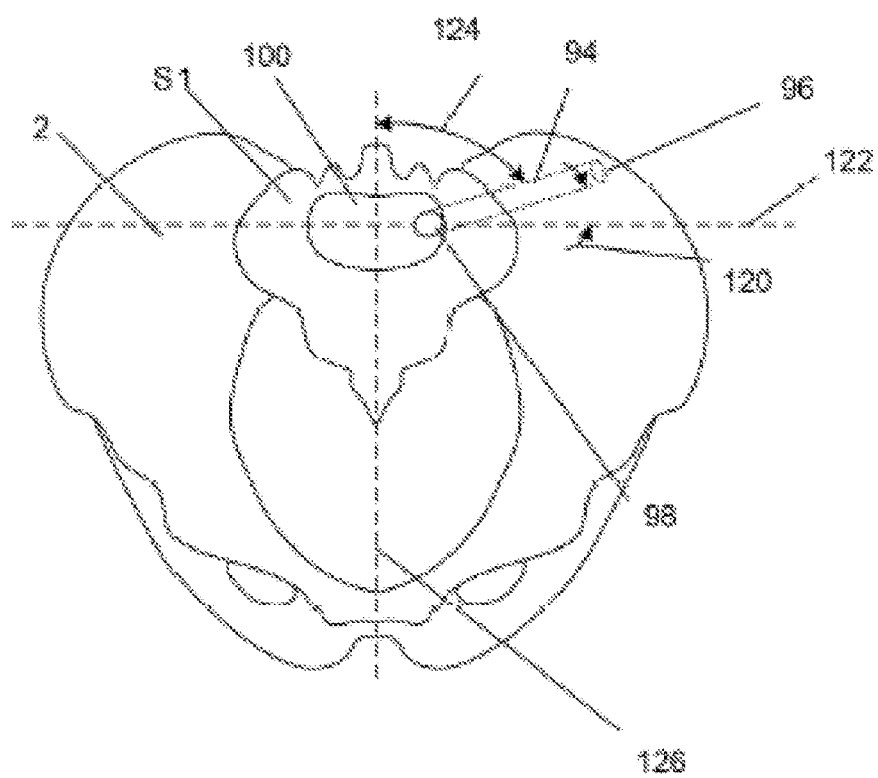
FIGS. 29 through 31 illustrate views through the transverse plane from a superior location, the sagittal plane from a lateral location, and the coronal plane from an anterior location, respectively, of a variation of the location of the transosseous delivery channel.
Figure 30:
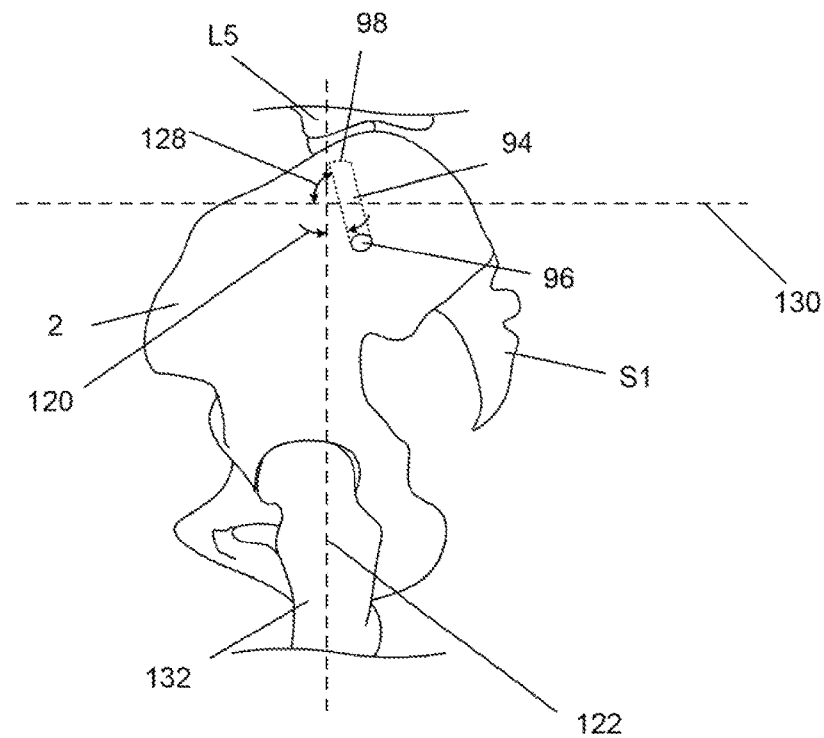
Figure 31:
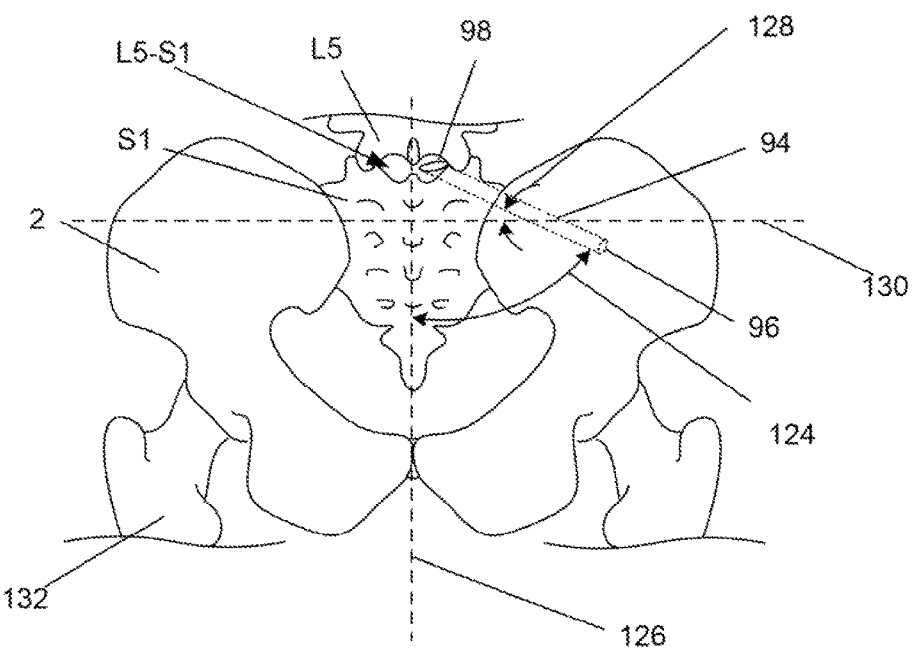
Figure 32B:
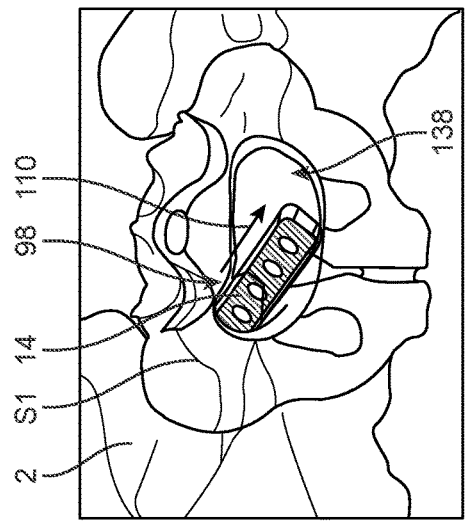
FIGS. 32a through 32d illustrate a superior view of a variation of a method of delivering the device showing the iliac and sacrum, but not the L5-S1 disc or remainder of the spine for illustrative purposes.
Figure 32D:
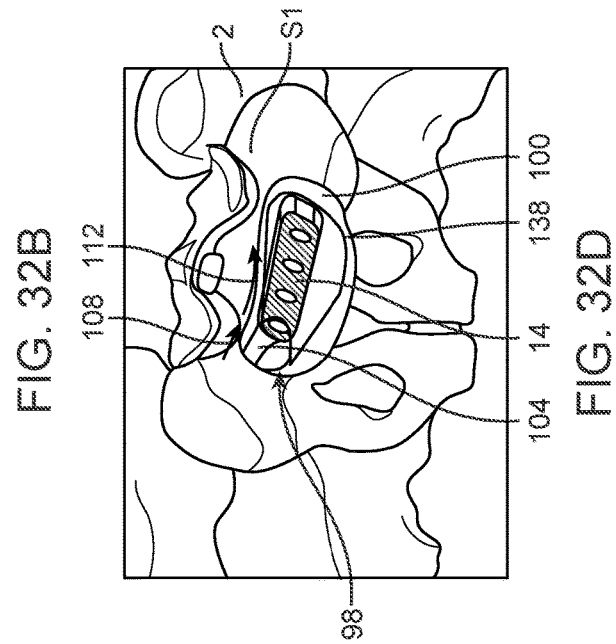
Figure 32A:
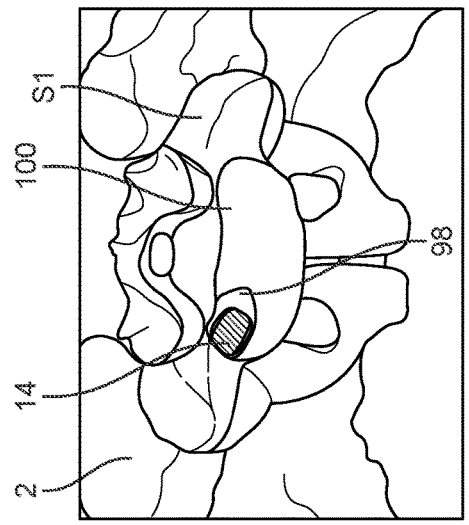
Figure 32C:
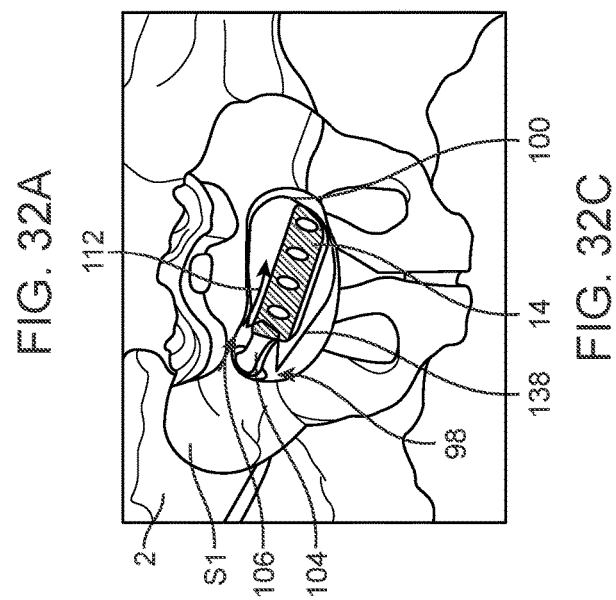

FIGS. 29 through 31 illustrate that the transosseous delivery channel 94 can have a coronal delivery angle 120 measured to the coronal plane 122, a sagittal delivery angle 124 measured to the sagittal plane 126, and a transverse delivery angle 128 measured to the transverse plane 130. The coronal delivery angle 120 can be from about 0° to about 25°, for example about 12°. The sagittal delivery angle 124 can be from about 65° to about 90°, for example about 75°. The transverse delivery angle 128 can be from about 0° to about 20°, for example about 10°. The support device 14 and shaft 104 can be configured so the support device 14 can exit the channel exit port 98 (e.g., directly into the L5-S1 intervertebral disc) and articulate sufficiently to enter and pass through all or a significant portion (e.g., more than about 40%, yet more narrowly more than about 50%, yet more narrowly more than about 75%) of the width of the L5-S1 intervertebral space.

FIGS. 30 and 31 show one or both femurs 132 for illustrative purposes.

Figure 33A:
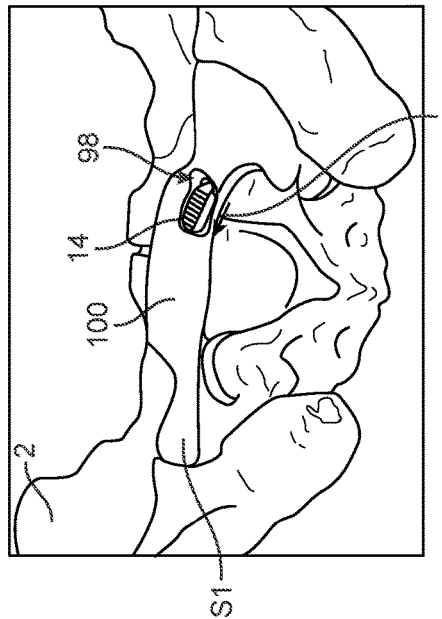
FIGS. 33a through 33d illustrate a posterior perspective view of a variation of a method of delivering the device showing the iliac and sacrum, but not the L5-S1 disc or remainder of the spine for illustrative purposes.
Figure 33B:
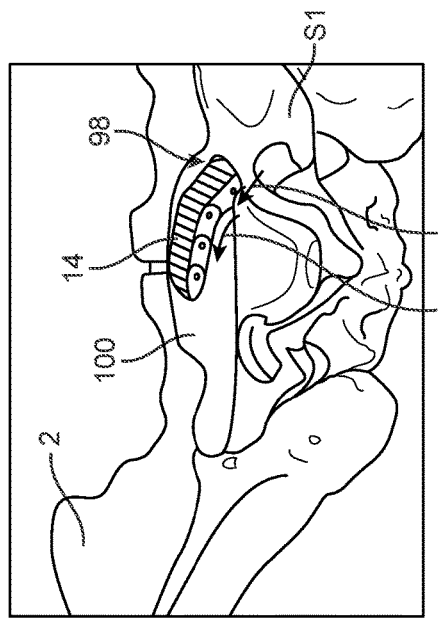
Figure 33C:
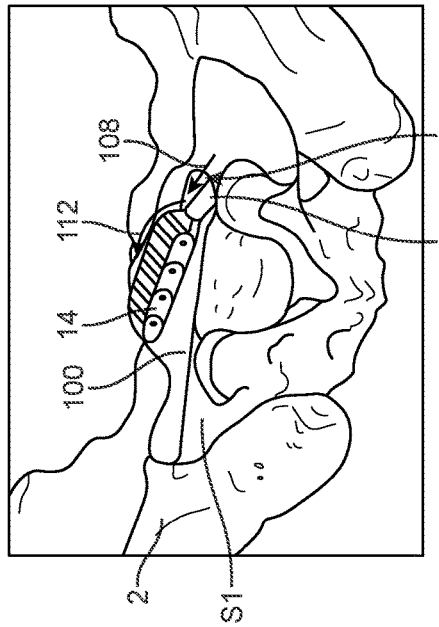

FIGS. 32a through 32d, and separately FIGS. 33a through 33c illustrate the deployment of the support device 14 into the L5-S1 intervertebral disc space target site, as described for FIGS. 24-27. The support device 14 can be delivered to a complete or partial discectomy target site 138 in the L5-S1 space.

Figure 33D:
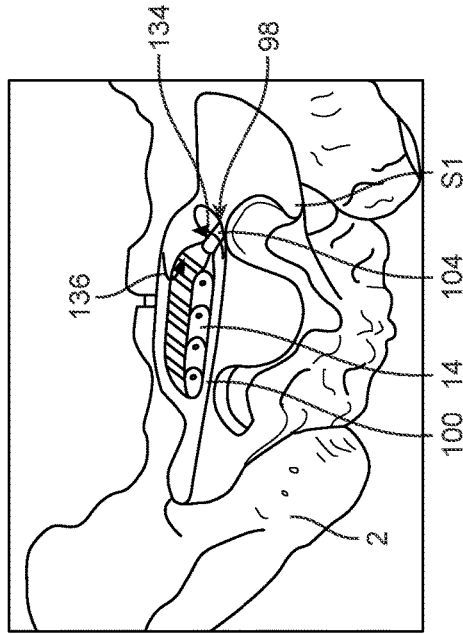

FIG. 33d illustrates the shaft 104 can be rotated, as shown by arrow 134, about the longitudinal axis of the shaft before during or after the support device 14 is positioned in the L5-S1 intervertebral disc space target site. The support device 14 can rotate, as shown by arrow 136, in the L5-S1 intervertebral disc space, for example to control and position the support device 14 to an angular orientation in the transverse plane 130.

Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the invention, and variations of aspects of the invention can be combined and modified with each other in any combination.

We claim:

1. A method for inserting an implant to a target site between a first vertebra and a second vertebra comprising:
    creating a first channel through an ilium, wherein at least a portion of a length of the first channel follows a shape of a medial surface of the ilium;
    creating a second channel through a sacrum, wherein the first channel is aligned with the second channel;
    inserting a first rigid section of an implant through the first channel and the second channel into a target site,
    rotating a second rigid section of the implant with respect to the first rigid section, wherein the first rigid section is hingedly attached to the second rigid section; and
    inserting the second rigid section of the implant into the target site.

2. The method of claim 1, wherein the second channel passes through a vertebral endplate.

* * * * *